US007878786B2

(12) United States Patent
Yost et al.

(10) Patent No.: US 7,878,786 B2
(45) Date of Patent: Feb. 1, 2011

(54) APPARATUS FOR PRODUCING TISSUE SCAFFOLD HAVING ALIGNED FIBRILS

(75) Inventors: Michael J. Yost, Lexington, SC (US); C. Michael Gore, West Columbia, SC (US); Louis Terracio, New York, NY (US); Richard L. Goodwin, Columbia, SC (US); Edie C. Goldsmith, Lexington, SC (US)

(73) Assignee: University of South Carolina, Columbia, SC (US)

( * ) Notice: Subject to any disclaimer, the term of this patent is extended or adjusted under 35 U.S.C. 154(b) by 111 days.

(21) Appl. No.: 12/072,150

(22) Filed: Feb. 25, 2008

(65) Prior Publication Data

US 2008/0220506 A1    Sep. 11, 2008

Related U.S. Application Data

(62) Division of application No. 10/861,664, filed on Jun. 4, 2004, now Pat. No. 7,338,517.

(60) Provisional application No. 60/475,680, filed on Jun. 4, 2003, provisional application No. 60/475,866, filed on Jun. 4, 2003, provisional application No. 60/475,986, filed on Jun. 4, 2003.

(51) Int. Cl.
*B29C 47/24* (2006.01)
(52) U.S. Cl. ..................... 425/71; 425/72.1; 425/73; 425/381; 425/461
(58) Field of Classification Search ............ 425/71, 425/72.1, 381, 381.2, 461, 466, 73, 74, 210
See application file for complete search history.

(56) References Cited

U.S. PATENT DOCUMENTS

| | | | | |
|---|---|---|---|---|
| 1,548,504 A | | 8/1925 | Becker | |
| 3,008,185 A | * | 11/1961 | Goldman | 264/559 |
| 3,114,372 A | | 12/1963 | Griset, Jr. et al. | |
| 3,114,593 A | | 12/1963 | Griset et al. | |
| 3,122,788 A | * | 3/1964 | Lieberman | 264/108 |
| 3,123,482 A | | 3/1964 | Lieberman | |
| 3,337,663 A | * | 8/1967 | Taga | 264/562 |
| 3,622,353 A | * | 11/1971 | Bradshaw et al. | 426/284 |
| 3,704,083 A | * | 11/1972 | Phipps | 425/71 |
| 3,842,151 A | * | 10/1974 | Stoy et al. | 264/203 |
| 4,060,081 A | | 11/1977 | Yannas et al. | |
| 4,138,503 A | | 2/1979 | Ziolko | |

(Continued)

OTHER PUBLICATIONS

Patent Cooperation Treaty (PCT) International Search Report (Form PCT/ISA/210), mailed May 26, 2005, completion date Apr. 21, 2005.

(Continued)

*Primary Examiner*—Yogendra N Gupta
*Assistant Examiner*—Joseph Leyson
(74) *Attorney, Agent, or Firm*—Dority & Manning, P.A.

(57) ABSTRACT

An apparatus for producing a tubular tissue scaffold having aligned biopolymer fibrils including a biopolymer gel dispersion feed pump that is operably connected to a tube-forming device having an exit port, where the tube-forming device is capable of producing a tube from the gel dispersion while providing an angular shear force across the wall of the tube, and a liquid bath located to receive the tubular tissue scaffold from the tube-forming device.

19 Claims, 8 Drawing Sheets

U.S. PATENT DOCUMENTS

| | | | |
|---|---|---|---|
| 4,536,365 A * | 8/1985 | Zwick | 264/558 |
| 4,544,516 A | 10/1985 | Hughes et al. | |
| 4,787,900 A | 11/1988 | Yannas | |
| 4,814,120 A | 3/1989 | Huc et al. | |
| 4,902,289 A | 2/1990 | Yannas | |
| 4,939,235 A * | 7/1990 | Harvey et al. | 528/337 |
| 5,171,273 A | 12/1992 | Silver et al. | |
| 5,277,857 A * | 1/1994 | Nicholson et al. | 264/187 |
| 5,378,469 A | 1/1995 | Kemp et al. | |
| 5,591,225 A | 1/1997 | Okuda | |
| 5,711,909 A | 1/1998 | Gore et al. | |
| 5,718,012 A | 2/1998 | Cavallaro | |
| 5,718,723 A | 2/1998 | Matsuda et al. | |
| 5,863,984 A | 1/1999 | Doillon et al. | |
| 5,972,441 A | 10/1999 | Campbell et al. | |
| 6,057,137 A | 5/2000 | Tranquillo et al. | |
| 6,090,117 A | 7/2000 | Shimizu | |
| 6,090,996 A | 7/2000 | Li | |
| 6,103,255 A | 8/2000 | Levene et al. | |
| 6,109,834 A | 8/2000 | Chitwood | |
| 6,124,256 A | 9/2000 | Hayry et al. | |
| 6,136,024 A | 10/2000 | Shimizu | |
| 6,245,099 B1 | 6/2001 | Edwin et al. | |
| 6,245,103 B1 | 6/2001 | Stinson | |
| 6,316,522 B1 | 11/2001 | Loomis et al. | |
| 6,323,022 B1 | 11/2001 | Chang et al. | |
| 6,331,422 B1 | 12/2001 | Hubbell et al. | |
| 6,337,198 B1 | 1/2002 | Levene et al. | |
| 6,365,149 B2 | 4/2002 | Vyakarnam et al. | |
| 6,371,992 B1 | 4/2002 | Tanagho et al. | |
| 6,391,333 B1 | 5/2002 | Li et al. | |
| 6,436,135 B1 | 8/2002 | Goldfarb | |
| 6,443,884 B1 | 9/2002 | Miyawaki | |
| 6,461,629 B1 | 10/2002 | Tranquillo et al. | |
| 6,471,993 B1 | 10/2002 | Shastri et al. | |
| 6,500,464 B2 | 12/2002 | Ceres et al. | |
| 6,517,571 B1 | 2/2003 | Brauker et al. | |
| 6,534,084 B1 | 3/2003 | Vyakarnam et al. | |
| 6,540,780 B1 | 4/2003 | Zilla et al. | |
| 6,544,762 B1 | 4/2003 | Tranquillo et al. | |
| 6,547,814 B2 | 4/2003 | Edwin et al. | |
| 6,554,857 B1 | 4/2003 | Zilla et al. | |
| 6,592,623 B1 | 7/2003 | Bowlin et al. | |
| 6,692,761 B2 | 2/2004 | Mahmood et al. | |
| 6,737,073 B2 | 5/2004 | Mahmood et al. | |
| 2003/0009151 A1 | 1/2003 | Wang | |
| 2004/0009600 A1 | 1/2004 | Bowlin et al. | |

OTHER PUBLICATIONS

PCT Invitation to Pay Additional Fees, mailed Feb. 11, 2005, International Application No. PCT/US04/17712, International Filing Date Jun. 4, 2004.

Patent Cooperation Treaty (PCT) "Corrected" International Search Report (Form PCT/ISA/210), mailed Jan. 13, 2006, completion date Apr. 21, 2005.

Nehrer S. et al. 1997. Canine chondrocytes seeded in type I and type II collagen implants investigated in vito. J. Biomed Mater Res (Appl Biomater) 38: 95-104.

* cited by examiner

FIGURE 6A
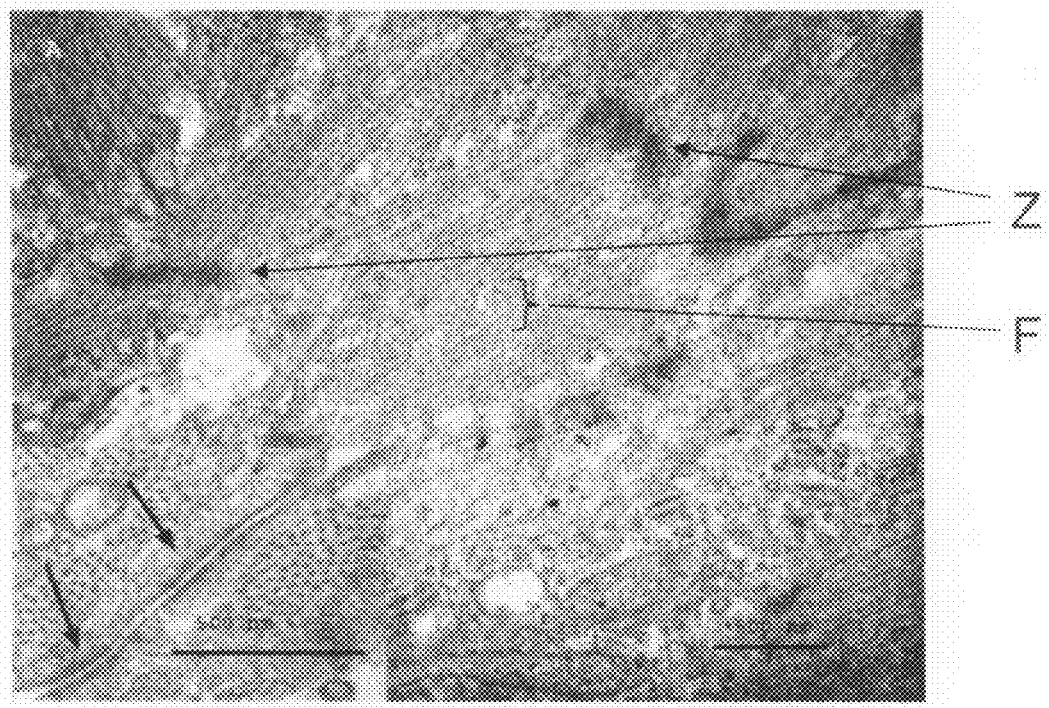
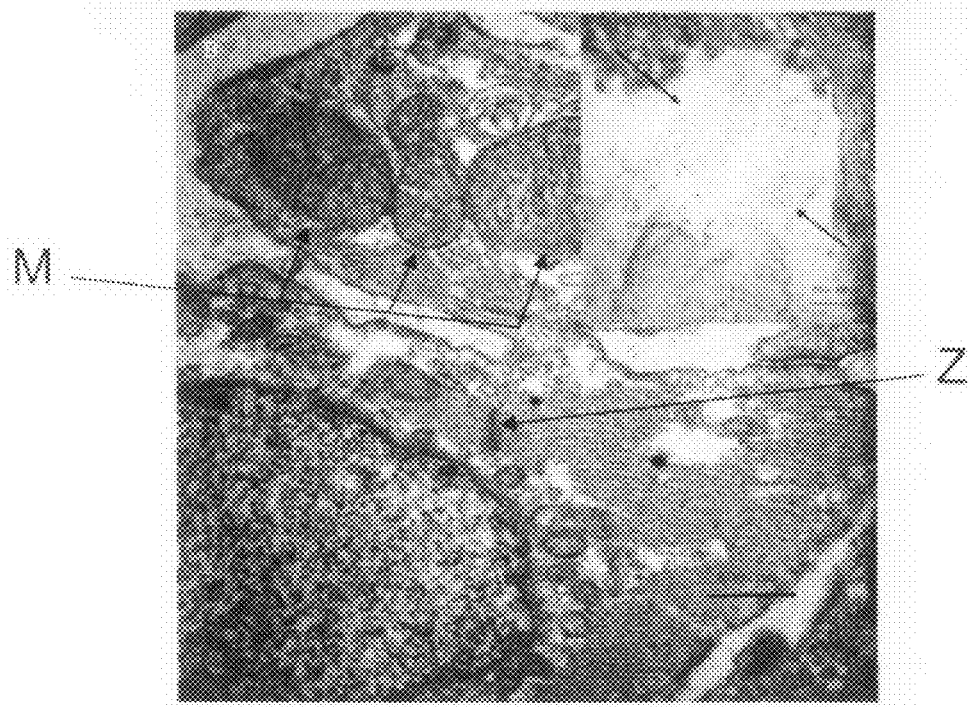
FIGURE 6B

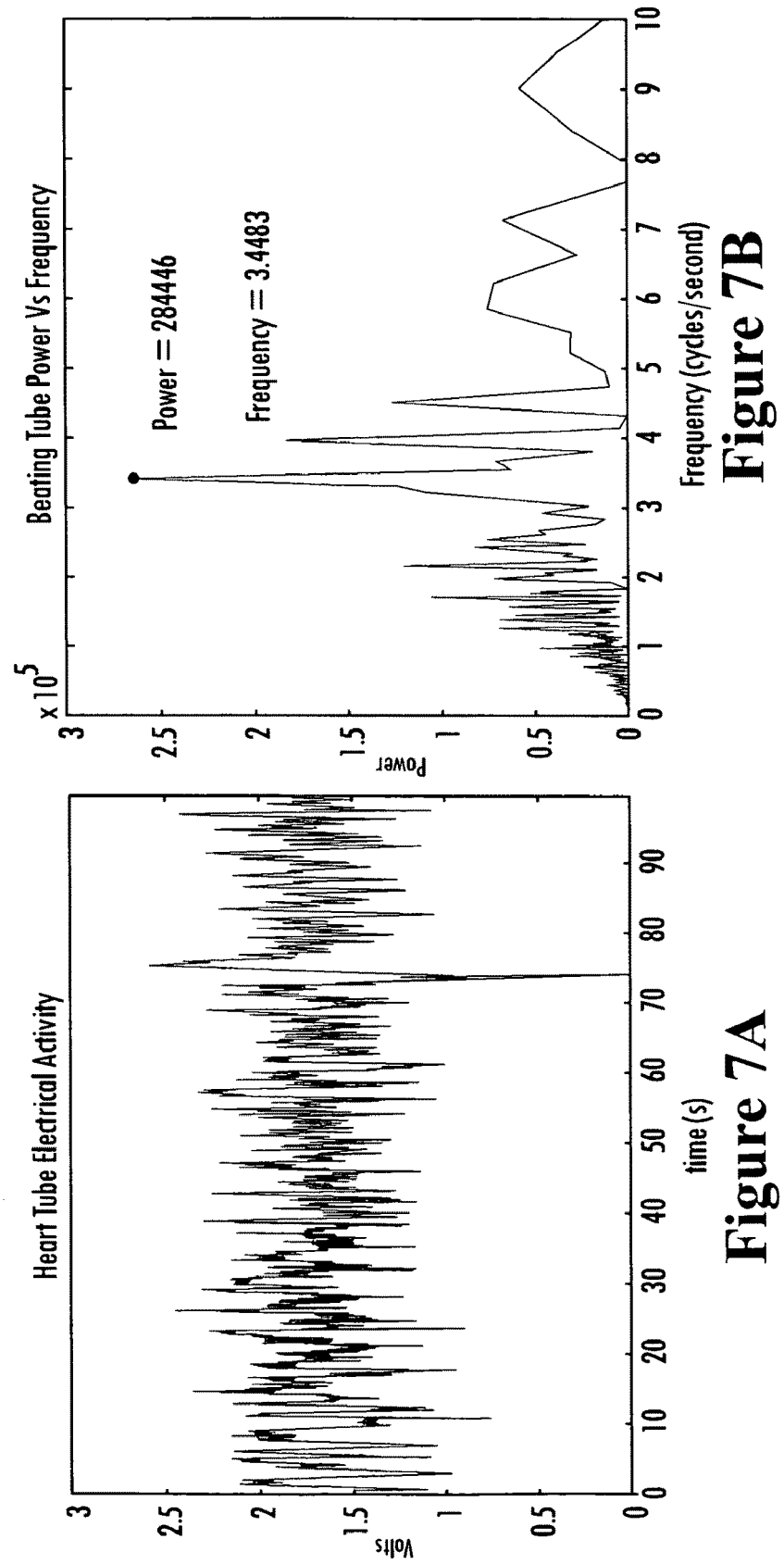

APPARATUS FOR PRODUCING TISSUE SCAFFOLD HAVING ALIGNED FIBRILS

CROSS REFERENCE TO RELATED APPLICATIONS

This application is a divisional application of U.S. Non-Provisional Patent Application Ser. No. 10/861,664, filed Jun. 4, 2004, now U.S. Pat. No. 7,338,517, which is related to and claims the priority benefit of U.S. Provisional Application Ser. Nos. 60/475,680; 60/475,866; and 60/475,986, filed Jun. 4, 2003, and each of which is incorporated herein by reference in its entirety.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of grant no. 1 K25 HL67097 awarded by the U.S. National Institutes of Health of the Department of Health and Human Services.

BACKGROUND OF THE INVENTION (1) Field of the Invention

The present invention relates to a tubular tissue scaffold, and, in particular, to a tubular tissue scaffold having aligned biopolymer fibrils, for use in tissue engineering applications; an apparatus and method of producing a tubular tissue scaffold having aligned biopolymer fibrils; and artificial tissue, and methods of use thereof, comprising living cells attached to a tubular tissue scaffold having aligned biopolymer fibrils.

(2) Description of the Related Art

The National Science Foundation defines tissue engineering as "the application of principles and methods of engineering and life sciences to obtain a fundamental understanding of structure-function relationships in novel and pathological mammalian tissues and the development of biological substitutes to restore, maintain, or improve [tissue] function." See Shalak, R. and Fox, J. eds., *Tissue Engineering*, Proceedings of a Workshop held at Granlibakken, Lake Tahoe, Calif., Feb. 26-29,1988, New York: Alan Liss (1988). In the last decade, over $3.5 billion dollars has been invested worldwide in tissue engineering research. More than 70 start-up companies or businesses having a combined annual expenditure of over $600 million dollars now participate in a significant engineering and scientific effort toward developing alternative sources of transplant materials through in vitro tissue engineering.

Several aspects of creating an engineered tissue make it a daunting task. One of the most difficult challenges is directing the behavior of specialized cells outside of the body to mimic the normal, endogenous phenotype those cells exhibit in vivo. Additionally, in order for an engineered tissue to be tolerated upon implantation, the material that provides the scaffolding for the cells must meet several important criteria. The material must be biocompatible, so as not to be toxic or injurious, and not cause immunological rejection. Also, the material must be biodegradable, by having the capability of being broken down into innocuous products in the body. Because cells respond biologically to the substrate on which they adhere, the materials that provide the growth surface for engineered tissues must promote cell growth. Further, the scaffolding material should be replaced by extracellular matrix components secreted by the grafted cells as the scaffold is broken down in the body. Additionally, the material should allow cells to grow and function as they would in vivo.

Initially, researchers adapted synthetic degradable polyesters that had been used in surgical materials since the early 1970s to construct scaffold materials for use in tissue engineering. These degradable polyesters include polyglycolide and polylactide, as well as the more recently developed polymer, polylactide coglycolide. However, those degradable polyesters tended to be inflexible, and their degradation in vivo has been associated with adverse tissue reactions. These shortcomings have led to the development of a host of new synthetic polymers, for example, polyhydroxybutyrate and copolymers of hydroxybutyrate with hydroxyvalerate. See Amass, W. et al., Polymer Int, 47:89-144 (1998).

In animals, collagens make up a majority of endogenous scaffolding materials. They are the most commonly occurring proteins in the human body and they play a central role in the formation of extracellular matrix. Collagens are triple-helical structural proteins. It is this triple-helical structure that gives collagens the strength and stability that are central to their physiological role in the structure and support of the tissues in the body. Although there are over twenty types of mammalian collagens, collagen types I, II, III, V, and XI make up the fibrous collagens. Type I collagen molecules polymerize into fibrils which closely associate in a parallel fashion to form fibers with enormous tensile strength, which are found in skin, tendon, bone and dentin. Type II is the major collagen found in cartilage, where the fibrils are randomly oriented to impart both stiffness and compressibility to the proteoglycan matrix. Type III collagen is found in skin, muscle, and vascular structures, frequently together with type I collagen.

Collagen has been used successfully in several tissue engineering applications. As a copolymer with glycoaminoglycans such as chondroitin 6-sulfate, collagen has been utilized as an artificial skin scaffold to induce regeneration in vivo for the treatment of burn injury since the early 1980s. See Burke, J. F., et al., *Ann Surg*, 194:413-28 (1981); Yannis, I. V., et al., *Science*, 215:174-6 (1982). Collagen has also been used to form anti-adhesion barriers for use on surgical wounds. See U.S. Pat. Nos. 5,201,745 and 6,391,939 to Tayot et al.; U.S. Pat. No. 6,451,032 to Ory et al. Zilla et al., in U.S. Pat. No. 6,554,857, describe the use of collagen, among other materials, as a component in a concentric multilayer ingrowth matrix that can have a tubular form.

However, some problems remain to be solved in the use of collagen as a scaffolding material for applications requiring structural and mechanical stability, such as for vascular prosthetics. This is at least partly due to an inability to isolate collagen possessing the physical properties required to maintain necessary mechanical integrity of a scaffold, as it is remodeled in vivo, for use in, for example, cardiovascular indications. Additionally, in order for a tubular construct to mimic endogenous components of the cardiovascular system, it must promote the proper growth, orientation, association, and function of specialized cell types.

Despite significant work in the field of tissue engineering and the numerous synthetic biomaterials that have been developed in the last decade, there is still a need for improved scaffolding materials for use in specialized applications. It would be useful, therefore, to provide a tissue scaffold in the form of a tube, comprising a biopolymer which promotes maintenance of an in vivo cell phenotype and, particularly, a tubular tissue scaffold that was non-toxic, biologically degradable in vivo, and causes little or no immune reaction in a host. It would also be useful to provide an apparatus and method for the production of such a tubular tissue scaffold. Also, despite the advances in biomaterials research, and the elucidation of the molecular biology of cell behavior and cell:matrix interactions, the gap between in vitro engineered tissue and biologically functional implantable organs remains significant. Therefore, it would be useful to provide artificial tissue that can act as a functional prosthetic. It would also be useful if the artificial tissue could be produced in the form of a tube, utilizing the tissue scaffolding described herein. This structural configuration would be particularly useful in cardiovascular applications.

SUMMARY OF THE INVENTION

Briefly, therefore, the present invention is directed to a novel tubular tissue scaffold comprising a tube having a wall, wherein the wall includes biopolymer fibrils that are aligned in a helical pattern around the longitudinal axis of the tube where the pitch of the helical pattern changes with the radial position in the tube wall.

The present invention is also directed to a novel apparatus for producing a tubular tissue scaffold having aligned biopolymer fibrils, the apparatus comprising a biopolymer gel dispersion feed pump that is operably connected to a tube-forming device having an exit port, where the tube-forming device is capable of producing a tube from the gel dispersion while providing an angular shear force across the wall of the tube, and a liquid bath located to receive the tubular tissue scaffold from the tube-forming device.

The present invention is also directed to a novel method of producing a tubular tissue scaffold, the method comprising:
 providing a gel dispersion comprising a biopolymer;
 feeding the gel dispersion to a tube-forming device that is capable of producing a tube from the gel dispersion while providing a radial shear force across the wall of the tube and having a gas channel connecting a gas source with the luminal space of the tubular tissue scaffold as it exits the tube-forming device;
 forming the gel dispersion into a tube; and
 causing the gel dispersion to solidify, thereby forming a tubular tissue scaffold comprising a tube wall having biopolymer fibrils that are aligned in a helical pattern around the longitudinal axis of the tube and where the pitch of the helical pattern changes with the radial position in the tube wall.

The present invention is also directed to novel artificial tissue comprising living cells attached to a tubular tissue scaffold comprising a tube having a wall, wherein the wall includes biopolymer fibrils that are aligned in a helical pattern around the longitudinal axis of the tube where the pitch of the helical pattern changes with the radial position in the tube wall.

The present invention is also directed to a novel method of preconditioning artificial tissue for implantation into the body of a subject, the method comprising: seeding a tubular artificial tissue scaffold having aligned biofibrils with living cells and culturing the cells in the presence of media containing at least one growth factor and under conditions where the tubular artificial tissue scaffold is subjected to stretch and pressure pulse of controlled frequency and amplitude.

The present invention also includes a novel preconditioned artificial tissue comprising living cells that are attached to a tubular artificial tissue scaffold having aligned biofibrils, wherein the cells have been cultured in the presence of media containing at least one growth factor and under conditions where the tubular artificial tissue scaffold is subjected to stretch and pressure pulse of controlled frequency and amplitude.

Additionally, the present invention provides a method of treatment comprising implanting in the body of a subject artificial tissue comprising living cells attached to a tubular tissue scaffold comprising a tube having a wall, wherein the wall includes biopolymer fibrils that are aligned in a helical pattern around the longitudinal axis of the tube where the pitch of the helical pattern changes with the radial position in the tube wall.

The present invention also encompasses a method of identifying the effects of a pharmaceutical composition on cell function comprising administering said pharmaceutical composition in vitro to artificial tissue comprising living cells attached to a tubular tissue scaffold comprising a tube having a wall, wherein the wall includes biopolymer fibrils that are aligned in a helical pattern around the longitudinal axis of the tube where the pitch of the helical pattern changes with the radial position in the tube wall.

Among the several advantages found to be achieved by the present invention, therefore, may be noted the provision of a tubular tissue scaffold having sufficient structural strength to withstand pressure; the provision of a scaffold having a composition that is biologically degradable in vivo and will result in a minimal immunological response from a host; the provision of a tissue scaffold having a structural composition that allows the penetration of cells and provides cells the requisite signals to develop an in vivo functional phenotype; the provision of an apparatus and a method for the production of such a tubular tissue scaffold, and; the provision of artificial tissue comprising cells attached to a tissue scaffold of biopolymer fibrils that is non-immunogenic, has a construction that mimics that of cardiac tissue, and has improved structural integrity.

BRIEF DESCRIPTION OF THE DRAWINGS

FIG. 6 shows transmission electron micrographs of cardiac myocytes on a collagen scaffold of the present invention. The micrographs demonstrate the presence of Z-bands (Z), aligned microfibrils (F), numerous mitochondria (M), cell: cell junctions (arrows in inset A), and interaction with collagen in the tube wall (arrows in inset B);

FIG. 7 shows a representative electrical signal obtained from a tubular scaffold of the present invention seeded with neonatal cardiac myocytes in panel (A), and Fast Fourier transform analysis of the electrical data in panel (B)

DETAILED DESCRIPTION OF THE PREFERRED EMBODIMENTS

Figure 1A:
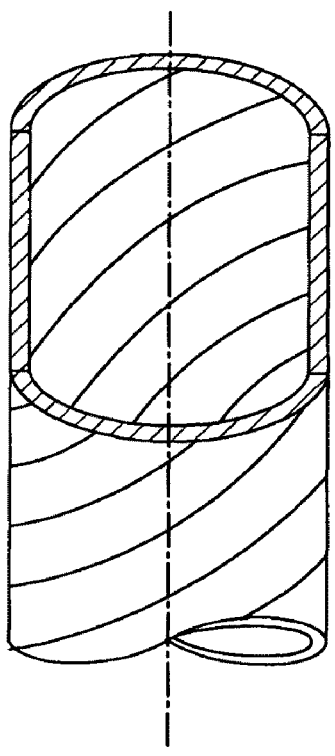
FIG. 1 is an illustration showing a partial cross-sectional cutaway view of a tubular tissue scaffold of the present invention illustrating helical alignment patterns of different direction of biopolymer fibrils at the luminal surface (left-hand pitch) and outside surface (right-hand pitch) of the tube (A), and also showing three side views of tubular tissue scaffolds showing that the pitch of the helical alignment pattern of fibrils at the luminal surface (dotted line having an angle with the longitudinal axis of $\alpha_L$) and outside surface (solid lines having an angle with the longitudinal axis of $\alpha_O$) of the tube can be approximately equal, but opposite in direction (B), or unequal in pitch, but opposite in direction (C), and include the case where the biopolymer fibrils are aligned at zero pitch ($\alpha_O=0°$), at the outside wall in this case, while the biopolymer fibrils at another location in the tube wall (here, the luminal surface of the tube wall) are aligned in a right-hand pitch of angle $\alpha_L$ (D)
Figure 1B:
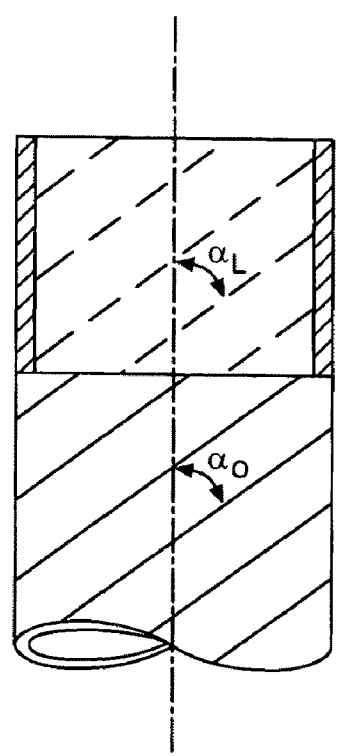
Figure 1C:
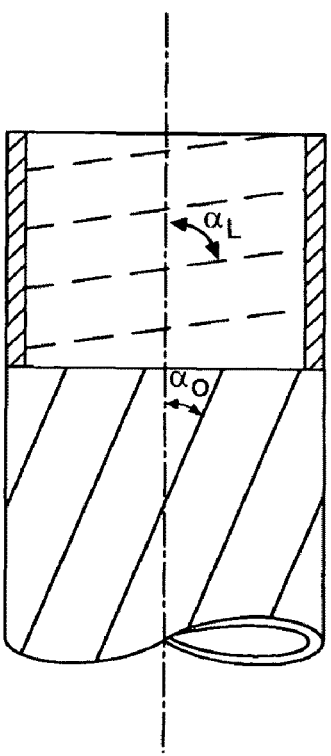
Figure 1D:
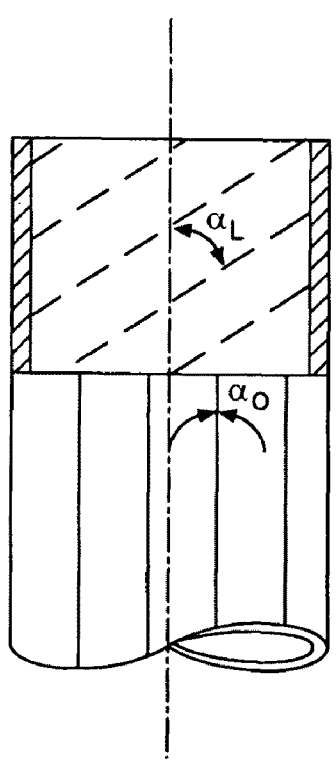

In accordance with the present invention, it has been found that a tubular tissue scaffold can be produced that comprises a tube wall which includes biopolymer fibrils that are aligned in a helical pattern around the longitudinal axis of the tube where the pitch of the helical pattern changes with the radial position in the tube wall, using a novel apparatus and method of producing such a tubular tissue scaffold. It has also been found that artificial tissue comprising living cells attached to the novel tubular tissue scaffold described herein can be produced and used to treat a variety of disease conditions by implanting the artificial tissue in the body of a subject.

The novel scaffold is unique in that it is not a very soft gel with little mechanical integrity, nor is it a tough highly crosslinked material resembling leather. In addition, toxic or potentially cytotoxic chemicals are not required to crosslink the scaffold material. Rather, the novel scaffold is made as an extruded tube with aligned biopolymer fibrils that impart biochemical and biomechanical information to cells that attach to them, which instruct the cells to adopt an in vivo—like phenotype.

The novel tissue scaffold provides the advantages that it has sufficient structural strength to maintain its tubular conformation without a support such as a mandrel, and can withstand at least about 12 mmHg internal pressure and in preferred forms can withstand pressures of at least about 280 mmHg, or more. The scaffold has a composition that will result in a minimal immunological response from a host; and the scaffold has a structural composition that allows penetration by living cells and provides cells the requisite signals to develop an in vivo functional phenotype.

From a mechanical standpoint, the properties provided by biopolymers that form fibrils give the scaffold a suitable modulus, suitable flexural rigidity, and a surface that is not too hydrophobic or too hydrophilic to support the cells and fluid necessary to form a tissue. Moreover, the biopolymers are biodegradable, nontoxic and support the maintenance and synthesis of new tissue. Furthermore, the present scaffold material will biodegrade at a controlled rate to allow new tissue to invade.

Pore size and distribution have been reported as important parameters for scaffold characterization and efficacy. See Dagalakis, N. et al., *J. Bio Med Matl Res.* 14(4):511 (1980), and Zeltinger, J. S. et al, *Tissue Engineering.* 7(5):557 (2001). The present tissue scaffold material is porous, with most pores between 1 and 10 µm in diameter. Although the average size of cells such as neonatal rat cardiac myocytes, for example, is 15-18 µm, it is believed that pore size is not a limiting factor that prevents myocyte penetration into the present scaffold material, since cells can remodel and create an appropriate extracellular matrix material if placed in the right environment. Pore size in the novel tissue scaffold material is discussed further below.

The present tubular tissue scaffolds provide biopolymer fibrils that are aligned in the tube wall in a helical fashion around the longitudinal axis of the tube. It is important, however, that in the present scaffolds the pitch of the helical pattern of the aligned fibrils changes as the radial location in the tube wall progresses from the inside (luminal) surface of the tube wall to the outside (or, outer) surface of the tube wall. In some embodiments, this pattern of fibril alignment can be characterized as being in a "corkscrew" pattern at the luminal wall of the tube and changing to a "counter-corkscrew" pattern at the outside wall of the tube. In other words, if fibril alignment on the luminal surface is in a right-hand helical pitch, the fibril alignment on the outside surface of the tube would be in a left-hand pitch, or vice-versa. This pattern mimics the extracellular matrix pattern of heart tissue, and, in one embodiment, allow the construction of more biologically-similar vascular constructs and heart constructs. By way of example, when the tissue scaffold is used to support the growth of neonatal cardiac myocytes, the myocytes can be made to constrict simultaneously, thereby twisting the tube while reducing its diameter, and thereby "wringing" fluid from the tube in a motion similar to that of a biological heart.

The present tubular tissue scaffold differs from previous constructs, such as those described in U.S. Pat. No. 6,540,780 to Zilla et al., which describes synthetic vascular grafts with helically oriented ingrowth channels within the tube wall, and U.S. Pat. No. 6,554,857 to Zilla et al., in that the present tubular tissue scaffolds comprise biopolymer fibrils that are aligned in a helical pattern within the tube wall. In Zilla et al. '780, only synthetic polymers are used, and both of these patents describe constructs where it is the ingrowth channels that are aligned within the tube wall, rather than biopolymer fibrils. In order to obtain the present tubular scaffolds, it is necessary to form the tube wall in a manner that imposes an angular shear across the tube wall as it is being formed, as is described below. The present tubular scaffolds, in fact, are substantially free of helically oriented channels within the tube walls.

When discussing the geometry of a tubular scaffold herein, the axis along the center of a cylindrical tube will be referred to as the longitudinal axis. The axis that is perpendicular to the longitudinal axis and runs outward from the center of the tube in a direction that is perpendicular to the tube wall is referred to as the radial axis. The helical pattern of the aligned biopolymer fibrils within the tube wall is described in terms of the "pitch" of the helix. As in the description of screw threads, for example, the pitch of the helix can be "right hand" or "left hand". The pitch of the helical pattern formed by the aligned fibrils is described in terms of the angle ($\alpha$) between a tangent to the helix and a projection of the longitudinal axis of the tube (as shown, for example, in FIG. 1, of the present specification). The pitch of the helical pattern of the biopolymer fibers at the luminal (internal) wall of the tube is designated as $\alpha_L$ and the pitch of the helical pattern of the biopolymer fibers at the outside wall of the tube is designated as $\alpha_O$.

When it is said that the biopolymer fibrils are "aligned", it is meant that most of the fibrils in the same radial plane in a tube wall run roughly parallel to each other. It is not meant that every fibril must be parallel to every other fibril in the plane, but that a general alignment pattern must be discernable. Such fibril alignment is shown, for example, in FIG. 2. The fibrils of the present tubular tissue scaffold are preferably not isolated from each other in the wall of the tube, but, rather, are associated in sheets or areas containing dozens, if not hundreds or thousands of fibrils that are adjacent or touching and are associated and a part of the helical pattern of alignment.

The term "fibrils" is used herein to describe an association of several biopolymer molecules into a structure that appears fibrous with suitable magnification, as is typical for collagen and other selected biopolymers of biological origin. There is no particular size limit to the fibrils of the present invention, and both fibrils and small fibers are included in the term.

As used herein, the term "biopolymer" refers to a natural or synthetic polymer that is biologically compatible. Polymers that are biologically compatible are those which can be implanted into a living vertebrate subject without triggering a severe adverse immune reaction. Examples of biopolymers that can be used in the present invention include, but are not limited to, collagen, fibronectin, laminin, elastin, fibrin, proteoglycans, hyaluronan, and combinations thereof. In some embodiments, the biopolymer is a collagen, selected from the group consisting of type I collagen, type II collagen, type III collagen, type V collagen, type XI collagen, and combinations thereof. In one embodiment, the collagen is selected from the group consisting of type I collagen, type III collagen, and combinations thereof. In preferred embodiments, the biopolymer is type I collagen.

Biopolymers that have not been isolated or purified to some degree from their natural sources, however, are not included in the scope of the present invention. In other words, the present tubular tissue scaffold is not meant to include natural vessels, arteries, or other natural biological tubular structure.

Type I collagen is the most prevalent structural extracellular matrix protein in the human body. Collagen has the property of being able to direct cell behavior by signaling the cells to modify their growth, differentiation, intercellular contacts, and production of molecules such as collagen and other extracellular matrix proteins and cytokines. Additionally, cells are capable of recognizing and correctly modifying the collagen matrix to conform to their cellular requirements. These features allow cells introduced to a collagen scaffold to mimic their normal in vivo phenotype and organization. By way of example, cells such as myocytes introduced to the surfaces of the tubular scaffold would readily attach to the collagen, remodel the matrix, and develop intercellular connections.

The tubular tissue scaffold of the present invention comprises a tube having defined dimensions such as an outside diameter, a luminal diameter, and a wall thickness. The novel tubular tissue scaffold can have any dimensions and is not limited to any particular diameter or wall thickness.

In one embodiment, the outside diameter of the tubular tissue scaffold is between about 0.1 millimeter and about 100 millimeters. In some embodiments, the outside diameter is between about 0.5 millimeters and about 50 millimeters, or between about 1 and about 10 millimeters, or between about 4 and about 10 millimeters. In preferred embodiments, the outside diameter is about 5 millimeters.

The luminal diameter of the tubular tissue scaffold is smaller than the outside diameter of the tube and may be between about 0.1 millimeters and about 49 millimeters. In one embodiment, the luminal diameter is between about 0.4 millimeters and about 49 millimeters. In preferred embodiments, the luminal diameter is between about 4 millimeters and about 5 millimeters.

The thickness of the tube wall, along with the size of the lumen, determines the rate of diffusion of nutrients that are critical for cell growth from the outside of the tube to the luminal surface. The tube wall can be of any thickness that will provide properties that are suitable for the intended application. In one embodiment, the tube wall thickness is between about 0.05 millimeters and about 10 millimeters. In another embodiment, the wall thickness is between about 0.1 millimeters and about 5 millimeters. In preferred embodiments, the wall thickness is between about 0.1 millimeters and about 1 millimeter.

As has been described briefly above, the tube wall of the tubular tissue scaffold comprises a helical alignment of biopolymer fibrils, the alignment having a certain pitch in relation to the longitudinal axis of the tube. A purpose of the particular alignment of biopolymer fibrils of the present invention is to allow for the generation of a pumping, or "wringing" type of mechanical force in a tubular scaffold construct, given the introduction of the proper cells to the scaffold.

In the present invention, the pitch of the helical pattern of biopolymer fibrils on the luminal surface can be between about 0 degrees and about 89 degrees and the pitch of the helical pattern on the outer surface is between about 0 degrees and about 89 degrees, where the pitch of the fibrils at the luminal surface is different from the pitch of the fibrils at the outer surface of the tube. In one embodiment, the pitch of the helical pattern of the fibrils at the luminal surface is between about 18 degrees and about 62 degrees and the pitch of the helical pattern of the fibrils at the outer surface is between about 18 degrees and about 62 degrees, where the pitch of the fibrils at the luminal surface is different than the pitch of the helical pattern of the biopolymer fibrils at the outer surface. In preferred embodiments, the pitch of the helical pattern of the biopolymer fibrils at the luminal surface is between about 26 degrees and about 60 degrees and the pitch of the helical pattern of the biopolymer fibrils at the outer surface of the tube is between about 26 degrees and about 60 degrees, where the pitch of the fibrils at the luminal surface is different from the pitch of the fibrils at the outer surface. In another embodiment, the pitch of the helical pattern of the biopolymer fibrils changes in a linear manner through the thickness of the tube wall, and the change can be from a right-hand pitch to a left-hand pitch, or vice versa.

In one embodiment of the present invention, the tubular tissue scaffold has pores. One feature of pore size is the effect that it has on the ability of cells to invade the matrix. In preferred embodiments of the present invention in which a biopolymer, such as collagen, for example, is used, cells introduced to the scaffold are able to remodel the material as they would in vivo, enabling the cells to infiltrate the matrix. Pore size must also provide sufficient permeability for the diffusion of nutrients from the media in in vitro culture conditions. In preferred embodiments of the present invention, the size of the pores is from about 1 micron to about 20 microns. More preferably, the size of the pores is from about 2 microns to about 10 microns. Unless explicitly described to the contrary herein, pore size is expressed in terms of number average pore size.

In some embodiments of the tubular tissue scaffold of the present invention, the luminal surface and outer surface of the tube can support cell attachment and growth. In preferred embodiments, the tissue scaffold can direct the morphology of attached cells to align along the helical pattern of the biopolymer.

In addition to growth and attachment of cells at the luminal surface and/or the outer surface of the tube, it is sometimes desirable that growing cells penetrate and grow into the tube wall. In other words, that growing cells grow throughout the depth or thickness of the tissue scaffold material. An advantage of the present tissue scaffold is that cells are able to penetrate and grow throughout the entire thickness of the tube wall, and in preferred embodiments, the growing cells align with the general alignment of the biopolymer fibrils throughout the thickness of the wall. This provides for a construct of artificial tissue scaffold having changing alignment of biopolymer fibrils throughout the tube wall thickness and also having growing cells throughout the tube wall thickness that match the alignment of the biopolymer fibrils. This structure permits closer matching of the physical structure of the artificial tissue with that of normal cardiovascular tissue.

In one embodiment, the tissue scaffold of the present invention can be treated with UV radiation to crosslink the biopolymer fibrils making up the tissue scaffold to increase the strength of the scaffold, as measured by increased burst pressure. As used herein, the term "burst pressure" refers to the maximum amount of fluid pressure which may be applied to the tubular tissue scaffold internally without causing a rupture. Treatment with radiation will be further described below, but the inventors have found that treatment of tubular tissue scaffolds with UV radiation increases the strength of the artificial tissue scaffold. When the artificial tissue scaffold is in the form of a tube, its strength can easily be measured and expressed in terms of the "burst pressure". As used herein, the terms burst pressure mean the internal pressure at which a tube bursts. Treatment of a present tubular artificial tissue scaffold with UV radiation at a wavelength that is from about 250 to about 280 nm and an energy density of from about 100 to about 1000 $\mu w/cm^2$, is preferred. By way of example, treatment with UV radiation at a wavelength of 254 nm and an energy density of 500 $\mu w/cm^2$ for 140 minutes increased the burst pressure of the tubes to 280 mm Hg, as compared to untreated tissue scaffolds which have an average burst pressure of about 125 mm Hg.

In preferred embodiments, a tubular tissue scaffold of the present invention has a burst pressure of at least about 100 mm Hg, more preferably at least about 200 mm Hg, even more preferably at least about 250 mm Hg, and most preferably at least about 280 mm Hg.

In another embodiment, the present invention is directed to an apparatus for use in the production of a tubular tissue scaffold having aligned biopolymer fibrils, as described herein.

Figure 4:
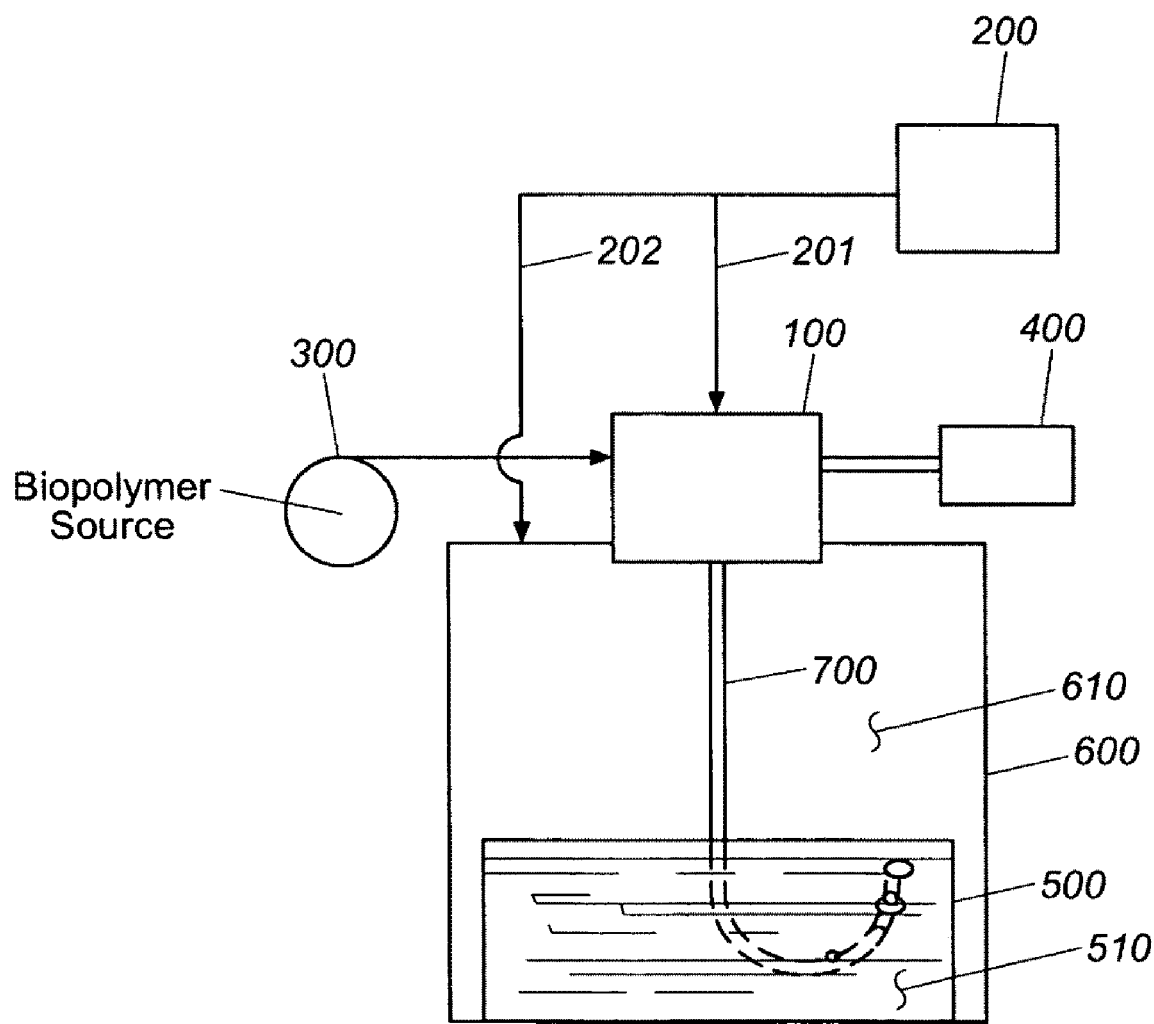
FIG. 4 is a schematic illustration of the major parts of an apparatus for producing a tubular tissue scaffold of the present invention.

The apparatus of the present invention can be described with reference to the figures. In FIG. 4 an apparatus for producing a tubular tissue scaffold having aligned biopolymer fibrils is illustrated. The apparatus comprises a gas source (200), which can be any type of source that can supply gas having a desired composition. It is preferred that the gas is a mixture of air and ammonia, and a mixture of air and ammonia in about a 50:50 mixture by volume is more preferred. A compressed gas cylinder is commonly used as a gas source, but the apparatus is not limited to such a source. The gas source (200) is operably connected to provide gas to a tube-forming device (100) through a conduit (201), and can, if desired, be operably connected to provide gas to a controlled atmosphere chamber (600) through a conduit (202). The gas source (200) can be used to supply gas to the luminal space of the tubular tissue scaffold (700), and, if desired, to the interior of the controlled atmosphere chamber (610). In a preferred embodiment, the controlled atmosphere chamber is filled with a gas mixture comprising air and ammonia, and a gas mixture comprising a mixture of about 50:50 air and ammonia by volume is more preferred.

A biopolymer feed pump (300) is operably connected to feed a biopolymer gel from a biopolymer gel source to the tube-forming device (100). The feed pump can be any type of liquid feeding device. Examples of suitable pumps are centrifugal pumps, gear pumps, peristaltic pumps, progressing cavity pumps, syringe pumps, and the like. It is preferred that the pump is one that is capable of feeding a viscous biopolymer gel (perhaps having a viscosity of from about 10 centipoise to as much as 1000 centipoise, or even more), at a metered rate, and under conditions where the cleanliness, and even sterility, of the biopolymer gel can be maintained. A syringe pump has been found to be useful for small scale tube-forming systems.

The tube-forming device (100) is one that is capable producing a tube from the gel dispersion while providing an angular shear force across the gel dispersion as it is formed into the wall of the tube. The tube-forming device (100) is preferably located so that the tubular tissue scaffold exiting the device (700) can easily be transferred to a liquid bath (500) located to receive the tubular tissue scaffold from the tube-forming device. The liquid bath contains a liquid that receives and cushions the extruded tube. The bath also serves to facilitate the solidification of the tube. In an embodiment, the liquid bath comprises water having sufficient ammonia absorbed therein to bring the pH of the water to between about 9 and 11, a pH of about 10 is preferred.

It is also preferred that the space between the exit of the tube-forming device (100) and the liquid bath (500) be enclosed to provide a controlled atmosphere chamber (600). In embodiments where the tubular tissue scaffold descends from the exit of the tube-forming device (100) to the liquid bath (500) by force of gravity, it is desirable that the surface of the liquid in the bath (510) be located a defined distance (L) below the exit of the tube-forming device.

In a preferred embodiment, the surface of the liquid bath is located between about 0.25 centimeter and about 60 centimeters below the exit port of the extruder, a distance of between about 2.5 centimeters and about 25 centimeters is more preferred, and a distance of between about 7.6 centimeters and about 16.2 centimeters is even more preferred.

Figure 3:
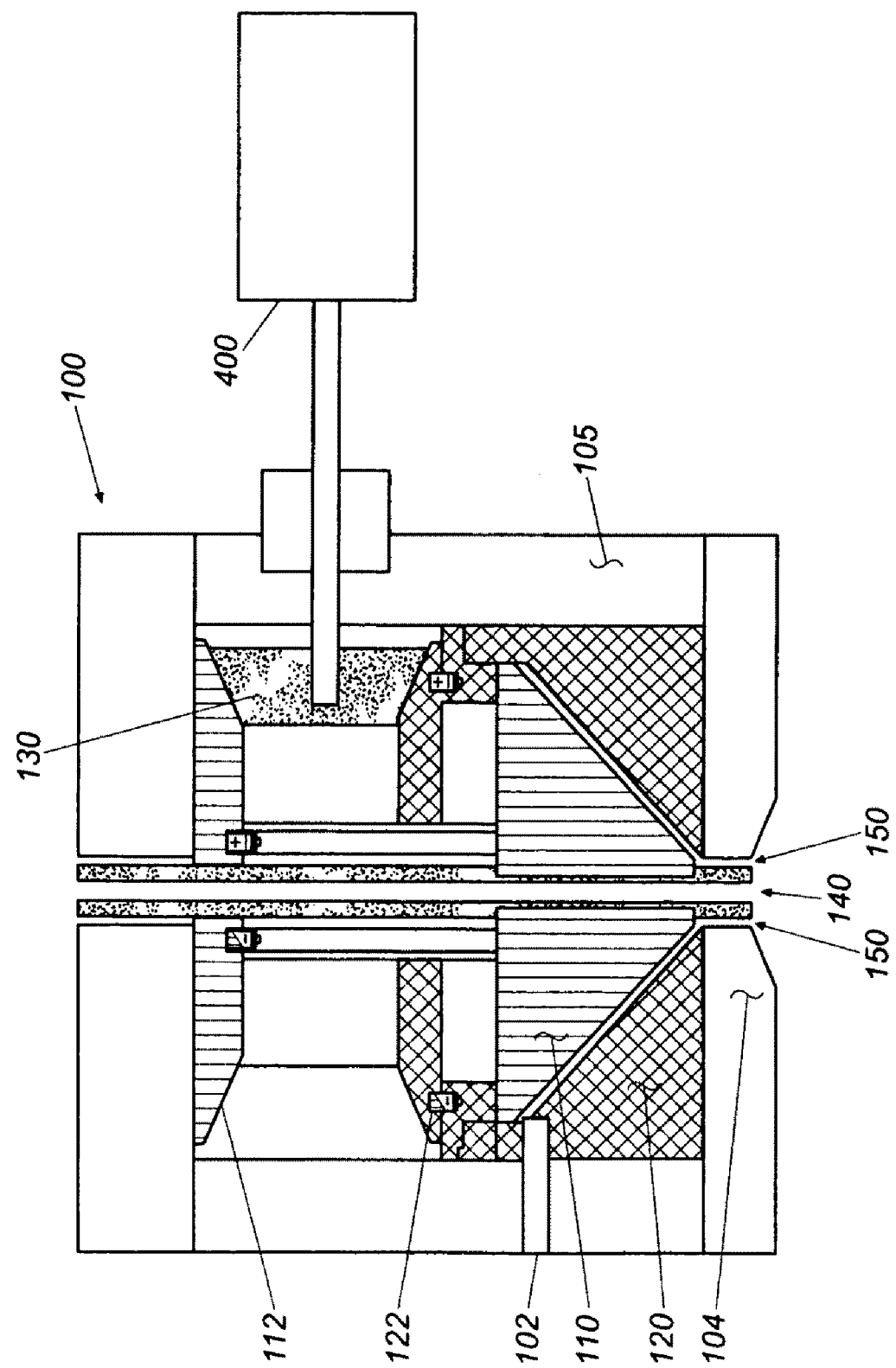
FIG. 3 is a sectional view illustrating the major parts of a counter rotating cone extruder of the present invention.

In a preferred embodiment, the tube-forming device (100) is a rotating cone extruder or a rotating disk extruder. In a yet more preferred embodiment, the tube-forming device is a rotating cone extruder. In an even more preferred embodiment, the tube-forming device is a counter-rotating cone extruder. With reference to FIG. 3, the major parts of a counter-rotating cone extruder include a body (105) with cover plate (104), within which is contained an external rotating member (120) having a cone-shaped cavity therethrough and an internal rotating cone (110), which may also be referred to herein as an "internal member" or internal rotating member', and which fits within the cone-shaped cavity of the external rotating member. The internal cone-shaped member (110) is connected to and is driven through an internal member drive gear (112) and the external rotating member (120) is connected to and driven by an external member drive gear (122). Both the internal member drive gear (112) and the external member drive gear (122) can engage and be driven by a pinion gear (130) that is connected to and driven by a drive shaft from the drive motor (400). The external rotating member and the internal rotating cone can terminate near the apex of the cones to form an annular-shaped exit port (150).

The external rotating member (120) and the internal rotating cone (110) can be operably connected to one or more drive motors (400) that can spin the external rotating member and the internal rotating cone about a common axis but in opposite directions. In a preferred embodiment, the external rotating member and the internal rotating cone are operably connected to the same drive motor. In a preferred embodiment, the one or more drive motors can be adjusted to vary the speed at which the external rotating member and the internal rotating cone rotate. The drive motor(s) can be designed to rotate at any speed, but it is preferred that the motor(s) be designed so that the rotational speed of the external rotating member and the internal rotating cone can be varied between about 1 rpm and 1800 rpm.

The counter-rotating cone extruder of the present invention can be smaller than counter-rotating cone extruders that are in common use and are commercially available. One of the problems associated with the manufacture of a reasonably priced counter-rotating cone extruder is the provision of the intricate bearings needed to retain the alignment and spacing of the external rotating member and the internal rotating member. It has been found that bearings can be dispensed with if the external rotating member and the internal rotating cone of the extruder are constructed of a durable, bearing-quality polymer. In preferred embodiments, the external rotating member and the internal rotating cone are constructed of Delrin® acetal resin (available from Tri Star plastics, Reading, Pa.).

If desired, the annular exit port (150) of the extruder is interconnected with a gas source via a gas conduit (140) to provide for the addition of gas to the luminal space of a tubular tissue scaffold exiting the extruder.

When the tube-forming device is a rotating-cone extruder or a counter-rotating cone extruder, the annular-shaped exit port has an outside diameter and an inside diameter. The difference between the outside diameter and the inside diameter of the annular space defines the width of the annular space. The thickness of the wall of the tubular tissue scaffold is directly related to, but not equivalent to, the width of the annular space.

The outside diameter and the inside diameter of the annular space can be any desired dimension, but it is preferred that the outside diameter of the annular-shaped exit port is between about 0.5 mm and about 150 mm, and the width of the annular space is between about 0.1 mm and about 10 mm. It is more preferred that the outside diameter of the annular-shaped exit port is between about 1 mm and about 20 mm, and the width of the annular space is between about 0.1 mm and 2 mm. It is yet more preferred that the outside diameter of the annular-shaped exit port is between about 1 mm and about 10 mm, and the width of the annular space is between about 0.1 and 1 mm.

The present invention also includes a method of producing a tubular tissue scaffold, the method includes the provision of a gel dispersion comprising a biopolymer.

In addition to the isolated and purified biopolymer, or combination of biopolymers, the biopolymer fibrils that form the tube wall of the present tissue scaffold can be mixed with any other polymers, or other additives, that are useful for the formation of, or the performance of, the tubular tissue scaffold. For example, fillers, dyes, drugs, or any other useful and pharmacologically acceptable material may be added.

The biopolymer is prepared to form a gel dispersion prior to formation of the present tubular tissue scaffold. By way of example, a gel dispersion of type I collagen can be prepared by: a) washing bovine hide sequentially in water, water containing $NaHCO_3$ and surfactant, and water; b) contacting the hide with an aqueous solution containing $NaHCO_3$, $Ca(OH)_2$ and NaHS; c) washing the hide in water; d) treating the hide with an aqueous solution of $Ca(OH)_2$; e) rinsing the hide with water and trimming the hide of any remaining skin tissue and fat; f) placing the hide in an aqueous salt solution and adding hydrochloric acid solution until the pH is stable between about 6.0 and 8.0; g) washing the hide in water; h) placing the hide in an aqueous solution of acetic acid with or without pepsin; i) mixing and allowing the hide to swell; j) placing the swollen hide in a mill and processing into a gel dispersion; k) filtering the gel dispersion to remove undissolved particles; l) centrifuging the gel dispersion to remove small undissolved particles; m) adding salt to the gel dispersion in an amount sufficient to precipitate collagen from the gel dispersion; n) filtering the collagen precipitate and resuspending it in deionized water; o) adding a base to bring the pH of the collagen dispersion to a pH between about 6 and about 8; p) dialyzing the collagen dispersion against phosphate buffered saline solution or tris[hydroxymethyl]aminomethane buffer; q) resuspending the collagen in deionized water; r) centrifuging the collagen dispersion to concentrate solid collagen gel as a pellet; and s) resuspending the pellet in aqueous mineral acid or organic acid. When an organic acid is used, acetic acid is preferred. When the pellet is resuspended in acid, it is preferred that the collagen concentration is adjusted to between about 15-35 g/l, about 20 g/l is more preferred.

The concentration of the gel dispersion can be adjusted to contain about 2%-3%, by weight, solids by the addition of water. The gel dispersion can be fed to a tube-forming device that is capable producing a tube from the gel dispersion while providing an angular shear force across the wall of the tube. This device can be a counter-rotating cone extruder, a counter-rotating disk extruder, or a counter-rotating cylinder extruder that preferably has a gas channel connecting a gas source with the luminal space of the tubular tissue scaffold as it exits the tube-forming device.

When the terms "angular shear force" are used herein, what is meant is a shear force that is applied across the wall of the tube, and in a direction generally perpendicular to both the radial and longitudinal tubular dimensions. In other words, a shearing force from the luminal wall of the tube to the outer wall of the tube, or vice versa, in a circumferential direction—as provided, for example, be a rotating cone extruder.

The tube-forming device forms the gel dispersion into a tube, and the tube is then solidified, thereby forming a tubular tissue scaffold comprising a biopolymer having fibrils in the tube wall that are aligned in a helical pattern around the longitudinal axis of the tube and where the pitch of the helical pattern changes with the radial position in the tube wall. Often, the pitch of the helical pattern on the luminal surface of the tube is different from the pitch of the helical pattern on the outside surface of the tube.

The pitch of the helical pattern of the fibrils can be controlled by control of such variables as the feed rate of the biopolymer gel dispersion to the tube-forming device, the rate of shear imposed on the gel as the tube is being formed, and the degree of drawing or compression of the tube after formation, but before solidification. In some embodiments, where the tube-forming device is a counter-rotating cone extruder that has an external rotating member having a cone-shaped cavity therethrough and an internal rotating cone which fits within the cone-shaped cavity of the external rotating member, the external rotating member is driven to rotate in one direction at a speed of from about 1 to about 1800 rpm and the internal rotating cone is driven to rotate in the opposite direction at a speed of from about 1 to about 1800 rpm. In a preferred embodiment, the external rotating member is driven to rotate in one direction at a speed of from about 150 to about 900 rpm and the internal rotating cone is driven to rotate in the opposite direction at a speed of from about 150 to about 900 rpm.

In a preferred embodiment of the present apparatus, the biopolymer feed pump (300) can be adjusted to vary the rate at which biopolymer is fed to the tube-forming device. When the tube-forming device is an extruder and the liquid bath (500) is located at a defined distance (L) below the extruder exit port (150), the tubular tissue scaffold exiting the extruder (700) can fall into the bath by force of gravity. In this configuration, it is possible to control the conformation of the tube as it solidifies by controlling the biopolymer feed rate and the distance between the exit port of the extruder and the surface of the liquid in the bath (L). Because the tube exiting the extruder is still an unsolidified gel dispersion, the tube can be drawn or compressed—affecting the aligned helical pattern of the fibrils—or it can collapse, unless certain measures are taken to control the conformation of the unsolidified tube.

In order to prevent the tube from collapsing, a gas can be fed from the gas source to the luminal space of the tubular tissue scaffold as it exits the extruder. The flow rate of this gas can be controlled so that it provides an internal pressure inside the tube sufficient to prevent the collapse of the walls of the tube without causing undue expansion of the tube that would adversely affect the helical pattern of the aligned fibrils. When collagen is used as the biopolymer, it is preferred that the gas comprises a mixture of air and ammonia gas. Contact of the ammonia with the biopolymer dispersion causes the pH of the walls of the tube to raise quickly, thereby facilitating the solidification of the biopolymer gel. In preferred embodiments, the mixture of air and ammonia is about a 50:50 mixture by volume.

In order to further facilitate the solidification of the tube of biopolymer gel, the controlled atmosphere chamber can be filled with the same gas as is fed to the lumen of the tube and the outside surface of the tubular tissue scaffold is contacted with a mixture of air and ammonia gas as it exits the extruder. Solidification of the tubular tissue scaffold can also be facilitated by providing that the liquid of the liquid bath is composed of water having sufficient ammonia dissolved therein to raise the pH of the bath liquid to about 10.

As mentioned above, when the liquid bath is located beneath the exit port of the extruder, the conformation of the tube can be controlled as it solidifies by controlling the biopolymer feed rate and the distance between the exit port of the extruder and the surface of the liquid in the bath (L). This can be accomplished by feeding the biopolymer gel dispersion to the extruder at a defined feed rate, and the defined feed rate and the defined distance (L) are selected so that the gel dispersion solidifies to form a tubular tissue scaffold comprising a biopolymer having fibrils in the tube wall that are aligned in a helical pattern around the longitudinal axis of the tube and where the pitch of the helical pattern on the luminal surface of the tube is different from the pitch of the helical pattern on the outside surface of the tube.

In an embodiment where the outside diameter of the annular-shaped exit port is about 5 mm and the width of the annular space is about 0.5 mm, the defined feed rate can be controlled to be sufficient to provide a tube extrusion rate of about 150 cm/min. and the defined distance (L) is between about 10 cm and about 20 cm. The "tube extrusion rate" referred to is the linear rate of speed at which the tubular tissue scaffold exits the tube-forming device.

Although the tubular tissue scaffold can remain in the bath for any desired length of time, when the bath comprises aqueous ammonia having a pH of about 10, it is preferred to leave the tissue scaffold in the bath for about 10 min-20 min, and about 15 min. is more preferred.

In a preferred embodiment, the step of causing the gel to solidify can further include immersing the tube in an aqueous solution containing 0.3% sodium bicarbonate, percent by weight.

After the gel has solidified, the tube can be sterilized by exposure to sterilizing radiation. Gamma radiation and/or UV radiation can be used for this purpose. In some embodiments, the use of both gamma and UV radiation is preferred.

The tubular tissue scaffold of the present invention could be used, for example, as an implanted prosthesis. In and of itself, the scaffold could act as a growth substrate on which the cells of the subject in which it is implanted adhere, replicate, and reconstruct the injured tissue. Additionally, the tubular tissue scaffold could be seeded with specific cell types in vitro, cultured, and then implanted in a subject.

In another embodiment of the present invention, the tubular tissue scaffold is split along the longitudinal axis and opened to form a sheet. The sheet contains layers of aligned biopolymer fibrils, where the direction of the alignment changes in each successive layer. As with the tubular construct, the sheet could be seeded in vitro with specific cell types either before or after splitting. Applications for this type of tissue scaffold could include any application that requires a sheet-type of tissue, rather than a tubular structure. Sheet-type scaffold material can be used, for example, for the preparation of artificial skin to treat burn injury or surgical patches for internal application.

In another embodiment, the present invention encompasses artificial tissue comprising living cells attached to a tubular tissue scaffold comprising a tube having a wall, wherein the wall includes biopolymer fibrils that are aligned in a helical pattern around the longitudinal axis of the tube where the pitch of the helical pattern changes with the radial position in the tube wall.

In an alternative embodiment, when the tubular artificial tissue scaffold is split to form a sheet-type structure, the artificial tissue comprises a sheet having a thickness, wherein the material comprising the sheet includes biopolymer fibrils having an alignment that changes with the thickness of the sheet.

In the artificial tissue of the present invention, living cells may be introduced to the luminal and outer surfaces of the tubular tissue scaffold. As used herein, the terms "introduced", "seed", and "seeded" in reference to cells refer to the addition of cells to the tissue scaffold by providing the cells in a cellular suspension and supplementing the solution in which the tissue scaffold is incubating with the cellular suspension. By way of example, cells are isolated from a given source, such as neonatal rat hearts, and dispersed in a solution to form a cellular suspension having a certain cell density. A volume of cellular suspension is injected into the tubular tissue scaffold using an IV catheter. The tubes are placed in a rotating wall bioreactor and the reactor is filled with additional cell suspension. The tubes and cells are incubated at a rotation rate of 20 rpm with 5% $CO_2$ at 37 degrees Celsius for several days.

In some embodiments, the living cells align along the helical pattern of the biopolymer. "Aligned along the helical pattern of the biopolymer", as used herein, means oriented in parallel with the direction of the biopolymer fibrils. In preferred embodiments, the living cells establish intercellular and extracellular connections such as those found in vivo. These connections can include, for example, intercalated disks between distal ends of adjacent cardiac myocytes consisting of gap junctions that mediate electrical signaling between cells, adherens junctions and desmosomes between adjacent cells (cadherin interactions), and focal adhesions and hemidesmosomes (integrin-matrix interactions).

The living cells in the present invention are selected from the group consisting of myocyte precursor cells, cardiac myocytes, skeletal myocytes, satellite cells, fibroblasts, cardiac fibroblasts, chondrocytes, osteoblasts, endothelial cells, epithelial cells, embryonic stem cells, hematopoetic stem cells, neuronal cells, mesenchymal stem cells, anchorage-dependent cell precursors, and combinations thereof. For example, the living cells can be a combination of cardiac myocytes and cardiac fibroblasts. In some embodiments the living cells are contractile. As used herein the term "contractile" means having the ability to shorten in length due to mechanical alterations in intracellular structural proteins. In preferred embodiments, the contractile cells are cardiac myocytes.

Neonatal cardiac myocytes maintain some plasticity, as they undergo hyperplastic growth to reach maturity following birth. On a planar growth surface, neonatal myocytes exhibit a stellate morphology unlike that seen in vivo. Given more appropriate growth substrates in vitro, such as an oriented matrix of collagen or laminin, neonatal cardiac myocytes will align with and attach to the matrix, adopt a rod-shaped morphology, and form organized arrays of myofibrils. See i.e. McDevitt, T. C., et al., *J Biomed Mater Res*, 60:472-9 (2002). These cells can also form intercalated disks to allow for the conduction of electrical signals from one cell to the next, resulting in coordinated contractile activity similar to that seen in the intact myocardium of the heart. However, conventional 2-dimensional culture systems cannot sustain this activity indefinitely, and cells stop beating after two to three weeks.

The 3-dimensional structure of the scaffolding used in the present invention provides a more physiologically similar context than 2-dimensional conditions, allowing, for example, grafted cardiac myocytes to form intercellular and extracellular connections between successive layers, so that the tube can contract as an organ. Without being bound by this or any other theory, the inventors believe that the ability of the ventricle of the heart to contract in a manner which propels blood out of the intraventricular space and into the systemic circulatory system may rely on the unique geometric configuration of the collagen fibrils in the extracellular matrix to properly align the cells of the myocardium. Therefore, the purpose of the particular alignment of biopolymer fibrils of the present invention is to allow for the generation of the same type of mechanical force, given the introduction of contractile cells to the scaffold. Accordingly, in one embodiment of the present invention, the cardiac myocytes contract synchronously along the helical pattern of the biopolymer, thereby twisting the tube while reducing its diameter, and thereby "wringing" fluid from the tube in a motion similar to that of a biological heart.

The term "contract synchronously" as used herein in reference to cardiac myocytes, refers to the ability of an electrical signal to pass rapidly from cell to cell via gap junctions to couple the cells so that they contract in unison as a single functional unit.

In one embodiment, artificial tissue of the present invention has living cells attached to two or more tubular tissue scaffolds, which may preferably be in the form of concentric tubes. In some embodiments, the living cells attached to individual tubular tissue scaffolds are of different cell types. By way of example, in artificial tissue comprising three concentric tubular tissue structures, the inner tube is seeded with contractile muscle cells and endothelial cells, the central tube is seeded with extracellular matrix-producing fibroblasts, and the outer tube is seeded with contractile muscle cells and endothelial cells.

In another embodiment, the artificial tissue can be engineered to contain and release cytokines and other pharmacologic agents that affect cell proliferation, development, migration, differentiation, and/or activity, which are appropriate for the specific application of the tissue. As used herein, such cytokines and other pharmacologic agents are referred to as "growth factors", and include, without limitation, epidermal growth factor (EGF), fibroblast growth factor (FGF), erythropoietin (EPO), hematopoietic cell growth factor (HCGF), platelet-derived growth factor (PDGF), stem cell factors, bone morphogenic protein (BMP), fibronectin, transforming growth factor-beta (TGF-$\beta$), and neurotrophins.

Growth factors modulate and control the inception, rate, and cessation of the vital healing events that may be associated with surgical implantation of engineered tissue. Growth factors are polypeptides that modulate cellular function and regulate cellular growth. These peptides are extremely potent and, in very small quantities, are able to induce a specific cellular response. Three key growth factors known to be vital to the proper healing of damaged tissue are vascular endothelial growth factor, platelet derived growth factor and nerve growth factor.

Vascular endothelial growth factor, VEGF, is an extracellular signal protein that acts through the membrane bound tyrosine kinase receptor, VEGF receptor, to stimulate angiogenesis in vivo. A shortage of oxygen in practically any type of cell causes an increase in the intracellular concentration of the active form of a gene regulatory protein called hypoxia inducible factor I (HIF-1). HIF-1 stimulates transcription of the VEGF gene (and others). VEGF is secreted, diffuses through the tissue and acts on nearby endothelial cells. The response of the endothelial cells to VEGF includes at least four components. First, the cells produce proteases to digest their way through the basal lamina of the parent vessel. Second, the endothelial cells migrate toward the source of the signal. Third, the cells proliferate. Fourth, the cells form tubes and differentiate. Thus, endothelial cells create and line the lumen of the newly formed blood vessels in the tissue. These neovessels will not persist on their own. They will develop microaneurysms as well as other abnormalities that eventually rupture. These vessels rely on the recruitment of pericytes, from the vasculature, under the influence of signals from the endothelial cells, to further mature into competent blood vessels with the addition of vascular smooth muscle cells and extracellular matrix. The recruitment of pericytes, in particular, depends on PDGF secreted by endothelial cells.

Almost every cell in almost every tissue is located within 50-100 $\mu$m of a capillary. In the case of wound healing, for example, there is a burst of capillary growth in the neighborhood of the damage to satisfy the high metabolic requirements of the repair process. Local infections and irritations also cause a proliferation of new capillaries most of which regress and disappear when the inflammation subsides. In all of these cases, the invading endothelial cells respond to signals produced by the tissue that they invade. The signals are complex, but a key part is played by VEGF.

Platelet derived growth factor (PDGF) is an extracellular signal protein that acts through the membrane bound tyrosine kinase receptors, PDGF receptors $\alpha$ and $\beta$, to stimulate the survival, growth and proliferation of various cell types in vivo. PDGF stimulates chemotaxis and proliferation of fibroblasts and smooth muscle cells as well as collagen synthesis and collagenase activity.

Nerve growth factor (NGF) is an extracellular signal protein that acts through a membrane bound tyrosine kinase receptor, Trk A, to stimulate survival and growth of neurons. Cell growth and division can be controlled by separate extracellular signal proteins in some cell types. Such independent control may be particularly important during embryonic development when dramatic changes in the size of certain cell types can occur. Even in adult animals, however, growth factors can stimulate cell growth without affecting cell division. The size of a sympathetic neuron, for example which has permanently withdrawn from the cell cycle, depends on the amount of nerve growth factor secreted by the target cell it innervates. The greater the amount of NGF the neuron has access to, the larger it becomes. Concentrations of 250 ng/ml of NGF have been shown to cause migration of neurons through collagen gels in vivo.

Therefore, when vascularization and innervation of the artificial tissue of the present invention is required, the presence of growth factors such as those described above is necessary for these processes to proceed in vivo.

In order to provide a useful amount of one or more growth factors, and to control their release from the artificial tissue of the present invention, the tissue scaffolds of the present invention can be incubated with a growth factor, or combination of growth factors, and allowed to absorb the growth factor(s). Alternatively, growth factors may be incorporated into the biopolymer solution prior to formation of the tubular tissue scaffold. It should be appreciated however, that the present invention is not limited by any particular method of treating the tissue scaffold with a growth factor, and the invention is applicable to any such method now known or subsequently discovered or developed. Growth factors useful in the present invention include, but are not limited to, vascular endothelial growth factor (VEGF), epidermal growth factor (EGF), fibroblast growth factor (FGF), erythropoietin (EPO), hematopoietic cell growth factor (HCGF), platelet-derived growth factor (PDGF), nerve growth factor (NGF), transforming growth factors $\alpha$ and $\beta$ (TGF-$\alpha$ and TGF-$\beta$), or combinations thereof.

In one embodiment, the tissue scaffold can be UV irradiated in order to crosslink the biopolymer fibrils. Such irradiation can be administered before or after the addition of growth factors. In one embodiment, the tissue scaffold is irradiated after the addition of growth factors, but prior to cell seeding in order to crosslink the biopolymer fibrils after growth factor addition to the scaffold. While not wishing to be bound by this or any theory, the degree of crosslinking can control the rate at which growth factors are released from the tissue. For example, the tissue scaffolds can be exposed to UV radiation at a wavelength of 254 nm and an energy density of 500 $\mu w/cm^2$ for 140 minutes. When compared to tissue scaffolds not subjected to UV radiation, tissue scaffolds treated as described above have a slower rate of release of growth factors. Therefore, treatment of the tissue scaffolds with UV radiation can be used to modulate the release of growth factors once cells have been seeded on the scaffold, in turn regulating processes such as neovascularization and innervation of the engineered tissue.

The present invention also encompasses a method of treatment comprising implanting in the body of a subject artificial tissue comprising living cells attached to a tubular tissue scaffold comprising a tube having a wall, wherein the wall includes biopolymer fibrils that are aligned in a helical pattern around the longitudinal axis of the tube where the pitch of the helical pattern changes with the radial position in the tube wall.

The term "subject" for purposes of treatment includes any vertebrate. Preferably, the vertebrate is a human or animal subject who is in need of treatment for an injury, disease, or disorder of the type that can be treated by the use of artificial tissue. The subject is typically a mammal. "Mammal", as that term is used herein, refers to any animal classified as a mammal, including humans, domestic and farm animals, and zoo, sports, or pet animals, such as dogs, horses, cats, cattle, etc. Preferably, the mammal is a human. Additionally, the term "implanting in the body" refers to surgically inserting into the subject at the site of the injury, disease, or disorder being treated.

When it is said that the present artificial tissue can be used in treatment for an injury, disease, or disorder of the type that can be treated by the use of artificial tissue, such treatment can include, but is not limited to, replacement of vessels such as, for example, coronary arteries; repair and/or replacement of any other physiologic tubular structures, such as, for example, ureters, veins, lymph channels, GI tract components, and the like; repair of injured bone; repair of damaged nervous tissue as in, for example, spinal cord injury; or correction of impaired cardiac function caused by, for example, ischemic heart disease.

In one embodiment, the artificial tissue used in the method of treatment has living cells introduced to the luminal and outer surfaces of the tissue scaffold, and preferably the cells are aligned along the helical pattern of the biopolymer. The living cells in the present invention can be selected from the group consisting of myocyte precursor cells, cardiac myocytes, skeletal myocytes, satellite cells, fibroblasts, cardiac fibroblasts, chondrocytes, osteoblasts, endothelial cells, epithelial cells, embryonic stem cells, hematopoetic stem cells, neuronal cells, mesenchymal stem cells, anchorage-dependent cell precursors, and combinations thereof. In some embodiments, the living cells are selected from the group consisting of cardiac myocytes, skeletal myocytes, fibroblasts, cardiac fibroblasts, chondrocytes, osteoblasts, endothelial cells, epithelial cells, embryonic stem cells, hematopoetic stem cells, neuronal cells, mesenchymal stem cells and combinations thereof.

In one embodiment, the living cells of the present invention originate from the subject receiving treatment. Autologous grafts are far less susceptible to rejection, as they are not recognized as foreign and, hence, do not elicit an immune response in the subject. In preferred embodiments, cells taken from the subject are introduced to the tissue scaffold in vitro. The cells are cultured for the period of time necessary for the cells to degrade the original scaffold biopolymer and regenerate a matrix of secreted extracellular matrix proteins. Preferably, the cells are cultured in vitro for a period of time necessary for the cells to degrade and replace at least 25 percent of the original scaffold. More preferably, the cells are cultured for a period of time necessary for the cells to degrade and replace at least 50 percent of the original scaffold and, more preferably still, a period of time necessary for the cells to degrade and replace at least 75 percent of the original scaffold. The remodeled tissue scaffold is then constructed of proteins produced by the subject's own cells, and is therefore not recognized as a foreign substance that would induce an immune response in the subject.

It is preferred, in the present invention, that the living cells introduced to the tubular tissue scaffold establish intercellular and extracellular connections such as those found in vivo. In one embodiment, these living cells are contractile. In preferred embodiments the contractile cells are cardiac myocytes. As mentioned previously, the unique organization of the tissue scaffold of the present invention is able to guide the formation of an interconnected, contractile cell system, wherein the cardiac myocytes contract synchronously along the helical pattern of the biopolymer in a "wringing" motion to pump fluid through the lumen of the tubular tissue scaffold. The pumping action of the artificial tissue can be made to be directional by any one of several methods. For example, one-way valves can be placed on one or both sides of a contractile artificial tissue tube that result in directing the flow of fluid through the tube. Alternatively, one or more artificial tissue tubes can be located in series and controlled with one or more pacing devices in a manner that creates a peristaltic action to force fluid from one end of the tubular construct to the other.

Because the artificial tissue is able to act as a pump when contractile cells are present, this particular embodiment of the present invention can be used in the treatment of an injury, disease, or disorder that involves abnormalities in either cardiac output or vascular tone, or vascular blockage. In some embodiments of the present invention, these can include congestive heart failure, dilated cardiomyopathy, hypertrophic cardiomyopathy, infiltrative cardiomyopathy, ischemic heart disease, heart attack, heart failure, coronary artery disease, atherosclerosis, hypertension, chronic renal disease, cerebrovascular disease, carotid artery disease, and peripheral vascular disease.

For most in vitro or in vivo uses, the tubular scaffold used to make the artificial tissue of the present invention should be sterilized and treated with antibiotic and antifungal agents. By way of example, the tubular scaffolds can be sterilized by placing them in sterile Mosconas solution (0.14M NaCl, 0.0027M KCl, 0.012M $NaHCO_3$, $4.2\times10^{-5}$ M $NaH_2PO_4$, 0.0094M glucose) and exposing them to gamma radiation or ultraviolet (UV) radiation or both for up to 4 hours. Following UV treatment, fresh Marconas solution with 0.01 mg/ml gentamycin, 4 µg/ml Amphotericin-B, and 10 µg/ml fibronectin can be added to a culture dish containing the tubular scaffolds and the tubes can be incubated for 24 hours with 5% $CO_2$ at 37° Celsius.

The artificial tissue of the present invention provides a tubular cell-based prosthetic that would be particularly useful for repairing or replacing tube-shaped "organs", such as various sized blood vessels including coronary arteries and renal arteries, ureters, fallopian tubes, or nerve fiber conduits. If the cells of the present invention include contractile cells, such as cardiac myocytes, the tube as a whole can contract in a "wringing" motion, as dictated by the alignment of the cells along the helical pattern of the biopolymer fibrils. This type of contractile engineered construct could be used, for example, as a ventricular assist device to enhance cardiac contractility in a failing heart. Large versions of such a contractile tubular artificial tissue could be implanted near the heart to improve systemic circulation. Smaller versions could be implanted near vital organs to improve local perfusion. For example, contractile tubes could be transplanted in the renal arteries to increase renal perfusion and improve cardiac performance while unloading the heart. In another example, contractile tubes could be implanted in the common carotid artery inferior to the carotid sinus to improve brain perfusion. The contractile tubes could be used as replacement coronary arteries to provide both a blood conduit as well as improved local perfusion during diastole. Preferably, the contractile activity of this type of construct is controlled with a pacing device. As used herein, "pacing device" refers to any electrical device that can be used to maintain a particular rate of contraction, such as, for example, the implantable cardiac resynchronization device made by Medtronic, Inc., called InSync®.

One problem that has limited the application of artificial tissue, and in particular, artificial muscle tissue such as replacement cardiac muscle tissue, is that the tissue must be able to function immediately and accurately in the rigorous environment of the continuously cyclically-contracting heart. Such tissue cannot be allowed to significantly degrade and be remodeled in situ. Currently available scaffolds for tissue engineering undergo global remodeling once implanted in vivo. In order to avoid or reduce the degree of remodeling and consequent loss of strength and/or function of implanted artificial tissue, the present invention includes a method for preconditioning the novel tubular artificial tissue scaffold by seeding it with cells, such as fibroblasts, and stimulating the cells with a combination of matrix components, growth factors, and mechanical stimulation. Without being bound by this theory, it is believed that such stimulation can control fibroblast proliferation, matrix synthesis, matrix degradation and fibroblast apoptosis, among other parameters that are important for artificial tissue development.

When it is said that the preconditioning includes stimulation of the cells with matrix components, what is meant is the selection and control of the composition of the present artificial tissue scaffold and its physical structure, as have been discussed above. For example, variables such as the type of biopolymer that is used to produce the fibrils, and how and to what extent they are aligned, as well as the dimensions of the tubular scaffold, are included in the selection and control of matrix components.

Mechanical signals play an integral role in both directing myocytes to assume the distinctive cytoarchitectural features characteristic of differentiated myocytes as well as the arrangement of individual myocytes into an intact muscle. A primary developmental force in the heart is mechanical signaling resulting from contractile force as well as an increase in pressure and volume. See Terracio, L., et al., *In Vitro Cell Dev Biol*, 24:53-8 (1988). The regulation, expression, synthesis, and degradation of various contractile and regulatory proteins, as well as cell size, are influenced by mechanical stress. Accordingly, in one embodiment of the present invention, artificial tissue containing certain cells, such as contractile cardiac myocytes, is preconditioned by the application of mechanical stress before being implanted in the subject. What is meant by "preconditioned by the application of mechanical stress" is permitting cells to become accustomed to forces, such as stretch, normally found in the cardiovascular system in vivo, by subjecting the cells to these forces before introduction into the subject.

One method of applying mechanical stimulation to the artificial tissue scaffold is by culturing artificial cardiac myocyte-containing tissue in a pulsatile internal flow stretch bioreactor that mimics the action of a developing cardiovascular system. Stretch has been shown to up-regulate both matrix metalloproteinase production as well as the synthesis of new matrix. It is believed that the pulsatile internal flow and stretch mimics the action of a developing cardiovascular system.

Figure 8:
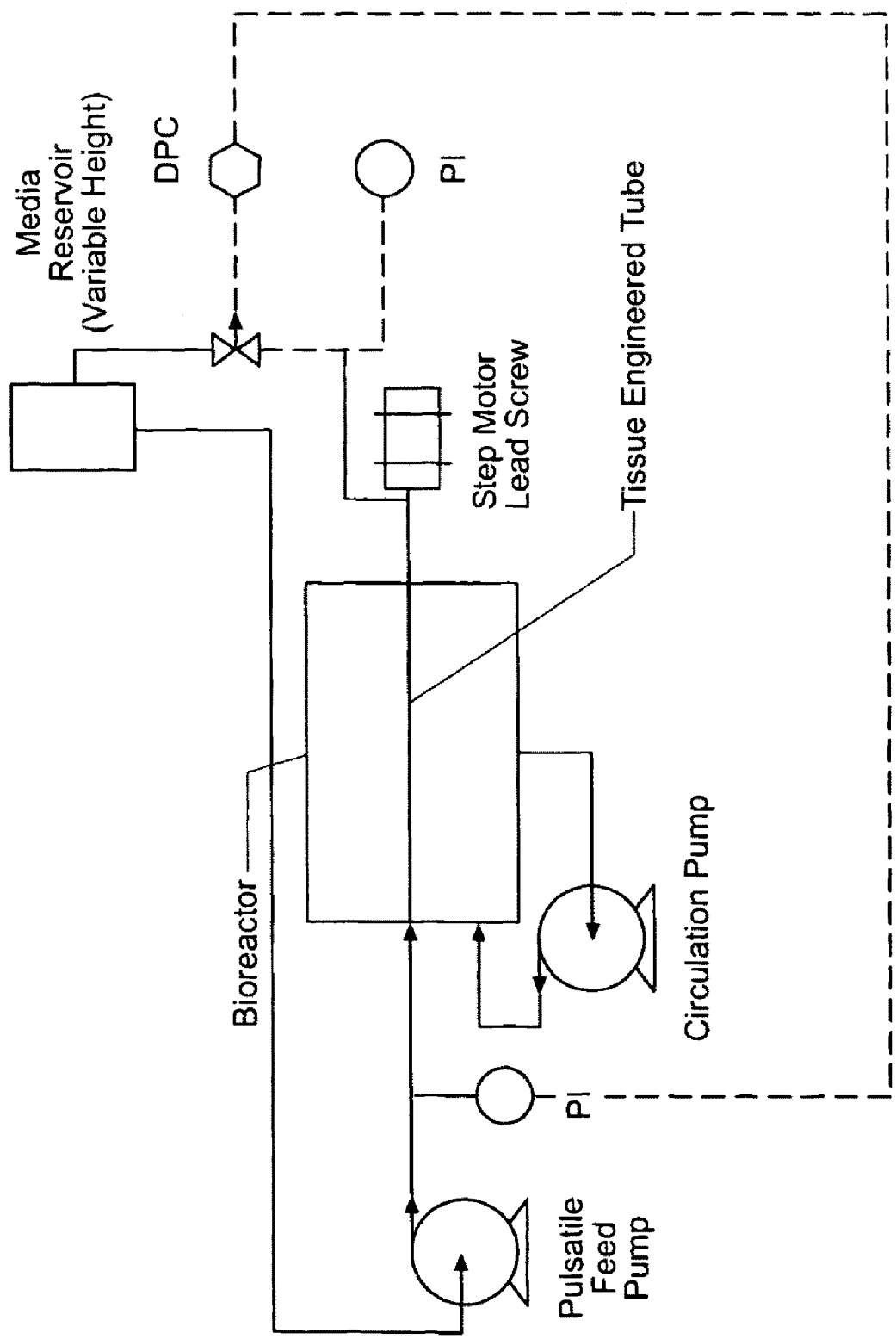
FIG. 8 shows a schematic illustration of a system including a pulsatile internal flow stretch bioreactor wherein the tubular tissue scaffold (tissue engineered tube) is attached at each end to supply and effluent tubing and media is fed through the tubing. A basal level of pressure is provided due to the height of the media reservoir and pulsed flow to cyclically stretch the cells. The bioreactor stretches the tubular scaffold both radially and longitudinally.

An example of a pulsatile internal flow stretch bioreactor is shown in FIG. 8. In this system, a tubular tissue scaffold, either before or after the attachment of cells is placed in the flow pattern of the bioreactor. The media reservoir can be adjusted to various heights from essentially zero height to a height equivalent to 10 cm of water pressure, or more. The pulse frequency and stretch frequency can be adjusted from 0 Hz to 2 Hz. It is believed that fibroblasts and myocytes that are seeded on the tubular tissue scaffold will remodel the matrix in response to the strain imposed by the pulse.

In addition to the presence of growth factors during the preconditioning process, other biologically active chemicals, such as matrix metalloproteinase (MMP) inhibitors can also be added in order to promote the preconditioning of the artificial tissue.

In one embodiment, the method for preconditioning the novel tubular artificial tissue scaffold comprises seeding a tubular artificial tissue scaffold having aligned biofibrils with living cells and culturing the cells in the presence of media containing at least one growth factor and under conditions where the tubular artificial tissue scaffold is subjected to stretch and pressure pulse of controlled frequency and amplitude.

The present invention also includes a novel preconditioned artificial tissue comprising living cells that are attached to a tubular artificial tissue scaffold having aligned biofibrils, wherein the cells have been cultured in the presence of media containing at least one growth factor and under conditions where the tubular artificial tissue scaffold is subjected to stretch and pressure pulse of controlled frequency and amplitude.

In another embodiment of the present invention, the tubular artificial tissue is split along the longitudinal axis and opened to form a sheet. The sheet contains layers of aligned biopolymer fibrils with attached cells, where the direction of the alignment changes in each successive layer. Applications for this type of artificial tissue could include, for example, artificial skin to treat burn injury or surgical patches for internal application. Cardiac myocytes seeded on a collagen sheet having the fibril alignment patterns of the present novel tissue scaffolds could provide functional myocardial patches to treat infarcted areas of the heart.

In one embodiment, the tubular tissue scaffold is split longitudinally and opened into a sheet prior to attaching living cells to the tissue scaffold. The sheet can be coated with an additional layer of biopolymer fibrils such as, for example, collagen, wherein the biopolymer fibrils polymerize and are oriented in the direction in which they are applied.

Living cells useful in this embodiment of the present invention include, for example, myocyte precursor cells, cardiac myocytes, skeletal myocytes, satellite cells, fibroblasts, cardiac fibroblasts, chondrocytes, osteoblasts, endothelial cells, epithelial cells, embryonic stem cells, hematopoetic stem cells, neuronal cells, mesenchymal stem cells, anchorage-dependent cell precursors, and combinations thereof. In preferred embodiments, the living cells are selected from the group consisting of myocyte precursor cells, cardiac myocytes, skeletal myocytes, satellite cells, fibroblasts, and combinations thereof. In one embodiment, the living cells originate from the subject receiving treatment.

The sheet form of the tissue scaffold can be used for treatment of, for example, hernia, heart attack, congenital heart defects, tissue missing due to congenital defect, skin burns, organ damage, and muscle damage.

In one embodiment, the sheet form of artificial tissue can be used to repair a tear or defect in a variety of tissues including, but not limited to, cardiac tissue, skeletal muscle tissue, epithelial tissue, vascular tissue, nerve tissue, lymphatic tissue, connective tissue, epidermal tissue, endocrine tissue, cartilage, and bone.

By way of example, the sheet form of artificial tissue can be used to repair a ventral hernia. Collagen tubes are produced as described herein, and are cut open longitudinally to form sheets. A thin layer of collagen solution can be streaked on the surface of the substrates and allowed to polymerize. This procedure results in a thin layer of collagen fibrils that are arrayed in parallel with one another along the direction that the collagen solution was streaked. Myocyte precursor cells such as, for example, satellite cells, can be introduced to the sheet scaffold and cultured until the cells differentiate into myocytes and fuse to form mature myotubes. This artificial skeletal muscle tissue can then be surgically applied to the damaged area of the abdominal wall to repair the hernia.

Additionally, the present invention embraces a method of identifying the effects of a pharmaceutical composition on cell function comprising administering said pharmaceutical composition in vitro to artificial tissue comprising living cells attached to a tubular tissue scaffold comprising a tube having a wall, wherein the wall includes biopolymer fibrils that are aligned in a helical pattern around the longitudinal axis of the tube where the pitch of the helical pattern changes with the radial position in the tube wall. Artificial tissue that has been made into sheet form as described above can also be used for the tissue scaffold for this method.

In one embodiment, the method further comprises determining the effects of a pharmaceutical composition on the cells by measuring or identifying changes in cell function. This can be accomplished by many methodologies known to those skilled in the art including, for example, Western blot analysis, Northern blot analysis, RT-PCR, immunocytochemical analysis, BrdU labeling, TUNEL assay, and assays of enzymatic activity. In some embodiments, the living cells are contractile cardiac myocytes. Accordingly, measurements of parameters such as isovolumic pressure generation, length tension, and isometric force generation can be made. By way of example, the instant artificial tissue containing cardiac myocytes that contract in culture could be treated with an agent, such as ephedrine, and any change in contractility of the myocytes can be measured as described in Example 3. This method provides an in vitro diagnostic system that can be utilized to rapidly assay the physiological consequences of administration of a given pharmaceutical composition on cell function such as, for example, cardiac contractility.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples all percentages are given on a weight basis unless otherwise indicated.

Example 1

This example illustrates the preparation of a biopolymer gel comprising type I collagen from a bovine steer hide.

Collagen was prepared from the hide of an 18-month old bovine steer by removal of the superficial epidermis including the hair and follicle pits. To isolate the collagen the hide was cut into 4×6 cm strips and washed with three changes of deionized (DI) water for 1 hr. each (the second wash contained 0.2% NaHCO$_3$). The remaining follicles and noncollagenous proteins were removed by bathing in a solution of 0.6% NaHCO$_3$, 2% Ca(OH)$_2$, and 4.3% NaHS for 30 min at 20° C. After three washings in DI water, the strips were treated overnight in 2% Ca(OH)$_2$ at 4° C. The remaining fat and epidermis were trimmed from the strips the following day. The strips were then placed in a 2M NaCl solution and neutralized with HCl to a pH of 6.8-7.0. The strips were then washed three times in DI water, cut into 0.5×2 cm pieces, and placed in a solution of 0.5 N acetic acid with or without pepsin, 1:100 based on hide weight. After incubating overnight at 4° C., the swollen strips were mixed with ice and emulsified into a gel dispersion using a Kitchen-Aid food processor (model # FP500WH; St. Joseph, Md.). The suspension was centrifuged at 9950×g for 35 min to remove small, unsolubilized particles. Type I collagen was precipitated from the gel dispersion by mixing with NaCl to a final concentration of 2M. The collagen was collected by centrifugation at 9950×g for 35 min, resuspended in DI water and neutralized to a pH of 7.2 using NaOH. The collagen suspension was then dialyzed vs phosphate buffered saline overnight and vs DI water for three changes over 24 hr. The resulting collagen gel was then centrifuged at 9950×g for 35 min to remove excess water and the collagen concentration adjusted to 25 mg/ml by addition of DI water and the pH adjusted to 2.5-3.0 with concentrated HCl.

Example 2

This example illustrates the production of a collagen tubular tissue scaffold having aligned fibrils by using a counter-rotating cone extruder.

Collagen tubes were produced by loading a collagen gel dispersion, produced as described in Example 1, into a 60 ml syringe that was placed into a syringe pump (having an adjustable feed rate of 0-20 cc/min) that fed the collagen into the feed port of a counter-rotating cone extruder that was fabricated from Delrin (Tri Star plastics, Reading, Pa.) according to the illustration shown in FIG. 1. The drive motor was a 90 volt 0.06 hp DC motor (Baldor Electric, Ft. Smith Ak.) with a regenerative feedback drive and a 5kΩ potentiometer for user interface (KB electronics, Coral Springs Fla.). The motor is coupled to the pinion gear which drives the outer rotating member and the inner rotating cone drive gears. The direct drive system can control speeds from 0 to 1800 rpm with a 2:1 reduction from the pinion gear to the drive gears. The extruder was mounted atop a controlled atmosphere chamber that consisted of a vented acrylic box that was purged at 1 L/min with a 50/50 mix of anhydrous ammonia and air.

As the dispersion was fed between the outer and inner rotating cones, a collagen tube exited through the annular-shaped exit port and was collected in a deionized water bath. The speed of the cone rotation and forward flow of the gel dispersion combined to create a helically aligned orientation pattern of the collagen fibrils. To maintain a lumen, as tubes are extruded, gas (air or air and ammonia) is metered between 10 to 60 ml/min through the tube. Following extrusion the tube was left in a water bath for 1 hr at room temperature followed by 30 min in a 0.3% $NaHCO_3$ solution and an additional 1 hr. in deionized water.

Determination of the Ditch of the Helical Pattern of the Aligned Collagen Fibrils:

By Polarized Light Microscopy:

To determine the pitch of the collagen fibrils at the outside and luminal walls of the tube, freshly extruded collagen tubes were fixed in 2.5% glutaraldehyde in phosphate buffered saline (PBS) for 1 hr at 25° C. The tubes were then stained with picrosirius red, and then imaged with a Bausch & Lomb Illuminator optical polarized microscope to examine the birefringent nature of the collagen fibrils. The lower polarizer was installed such that light was polarized in a north-south direction and the upper analyzer was oriented in the east-west direction.

Samples were placed on the rotary stage of the polarized light microscope in an east-west direction with respect to the long axis of the tube. The stage was rotated from 0° to 180° and the stage angle showing maximum darkness and brightness recorded. When the collagen fibers were at a 45° angle between the polarizer and the analyzer, transmitted light was at its maximum intensity and the collagen orientation could be directly visualized. When the pitch of the helical pattern coincided with either the lower polarizer or upper analyzer, the refracted light was quenched and there was minimal light transmission. The rotation angle of the stage was recorded at each interval of maximum and minimum light transmission and the angle of the fiber array calculated with respect to the long axis of the tube.

BY Scanning Electron Microscopy (SEM):

To further illustrate the helical orientation of the collagen fibrils in the tubes, samples were prepared for SEM by the O-GTA-O-GTA-O method of Takahashi et al., *J. Electron Microsc.*, 35(3):304 (1986). Extruded collagen tubes were fixed for 2 hr. in 3% glutaraldehyde in 0.1 M sodium cacodylate buffer (pH 7.4), rinsed in buffer, and immersed in 2% aqueous $OsO_4$ for 2 hr. After rinsing, samples were treated with two repetitions of GTA-O steps: 3×4 hr 8% glutaraldehyde/2% tannic acid at 4° C., rinse, 2 hr. 2% $OsO_4$. Tubes were then dehydrated in a graded ethanol, critical point dried, mounted on aluminum stubs and imaged on a JEOL JSM-6300V at 10 kV.

Figure 2:
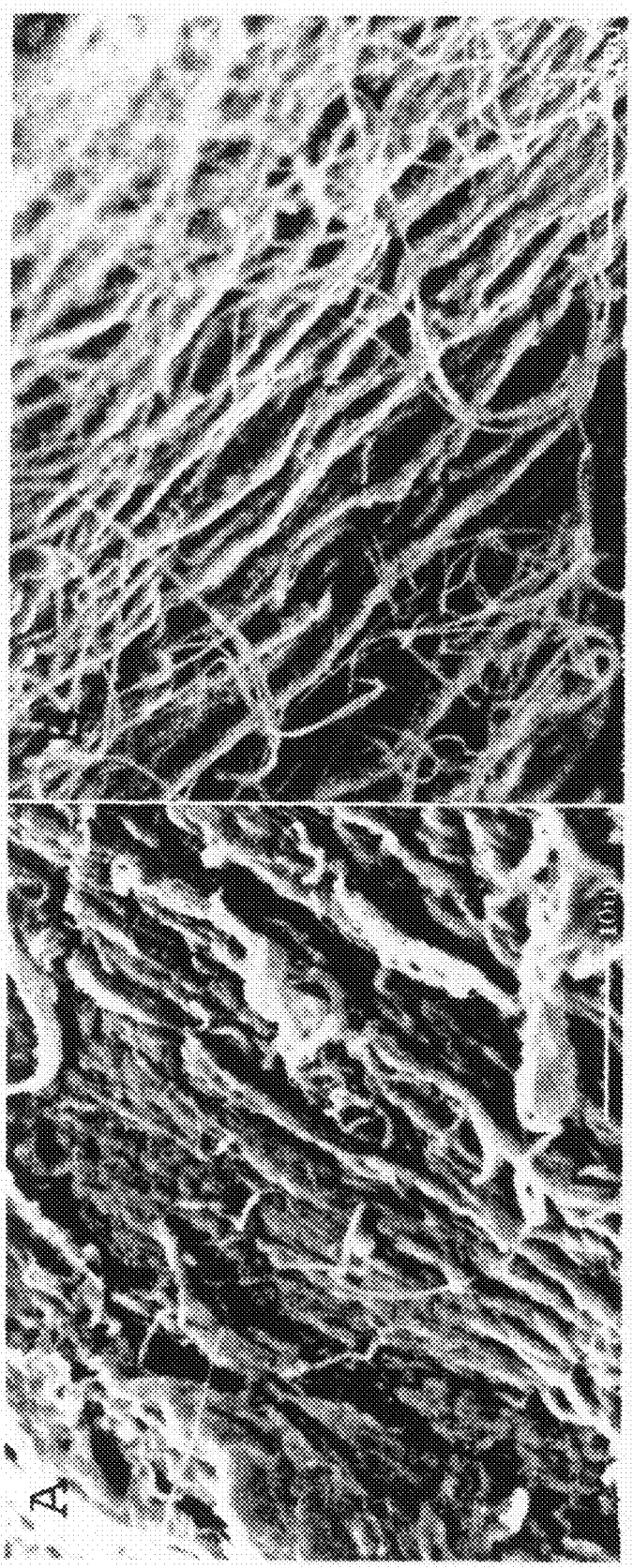
FIG. 2 shows scanning electron micrographs of the luminal and outside surfaces of a tubular scaffold of the present invention in which the longitudinal axis (along the center of the tube) is roughly vertical between the two images and where panel (A) shows the alignment of the collagen fibrils on the outside of the tube wall and panel (B) shows the reverse pitch orientation of the collagen fibrils on the luminal surface of the tube wall.

The counter rotating action of the extruder cones created a spiraling, or helical, alignment of the collagen fibrils that had a uniform direction on each of the outside and luminal walls of the tube. A section of a tube was split longitudinally down the tube wall and the tube was opened into a sheet. SEM microscopy of each side of the sheet is shown in FIG. 2 and clearly shows the "corkscrew" and "counter corkscrew" orientation of the fibrils at the surface of the outside and luminal tube walls. In this tube the pitch of each helix was about 45°, and in opposite directions.

When the cone rotation rate that varied from 150 rpm to 900 rpm at a fixed extrusion rate of 150 cm/min, the fibril angle of each array with respect to the long axis of the tube varied between 26° to 62°. Slower rotation speeds resulted in smaller angles while higher cone rotation speeds resulted in larger angles.

Example 3

This example illustrates seeding of cardiac myocyte on a collagen tubular tissue scaffold.

Collagen tubes were produced as described in Example 2. Prior to the addition of myocytes, the collagen tubes were sectioned into 1.25 cm lengths. The small collagen tube sections were placed in sterile Mosconas solution (0.14M NaCl, 0.0027M KCl, 0.012M $NaHCO_3$, $4.2×10^{-5}$ M $NaH_2PO_4$, 0.0094M glucose) and exposed to ultraviolet (UV) light for 4 hours to sterilize. Following UV treatment, fresh Marconas solution with 0.01 mg/ml gentamycin, 4 µg/ml Amphotericin-B, and 10 µg/ml fibronectin was added to a culture dish containing the collagen tube sections and incubated for 24 hours with 5% $CO_2$ at 37° Celsius.

Isolation of neonatal cardiac myocytes was performed as described by Simpson et al., *J Cell Physiol*, 161:89-105 (1994). For seeding, collagen tube sections were placed in 150 mm culture dishes and 0.5 ml of a cellular suspension containing $2×10^6$ cells/ml was injected into the lumen of each tube using an 18 gauge IV catheter (Surflo Terumo Mol. Corp., Somerset, N.J.). The tubes were then placed in a Synthecon Rotating Wall Bioreactor (Synthecon, Houston, Tex.) and the reactor filled with an additional 2.5 ml of cell suspension. Incubation was at a rotation rate of 20 rpm with 5% $CO_2$ at 37° Celsius for 72 hours.

Following incubation in the bioreactor, tubes were placed in culture dishes with fresh media containing 4 μg/ml cytosine β-D-arabino-furanoside. After 72 hours in the bioreactor, individual myocytes contracted spontaneously. Two further cell seedings were performed by adding $2\times10^6$ cells per tube to the tube lumen and outside surface at one week intervals. After 10 days in culture, entire areas of the tube contracted and, after 16 days in culture, synchronous myocyte contraction and forceful contractions of the entire tube were observed.

Figure 5A:
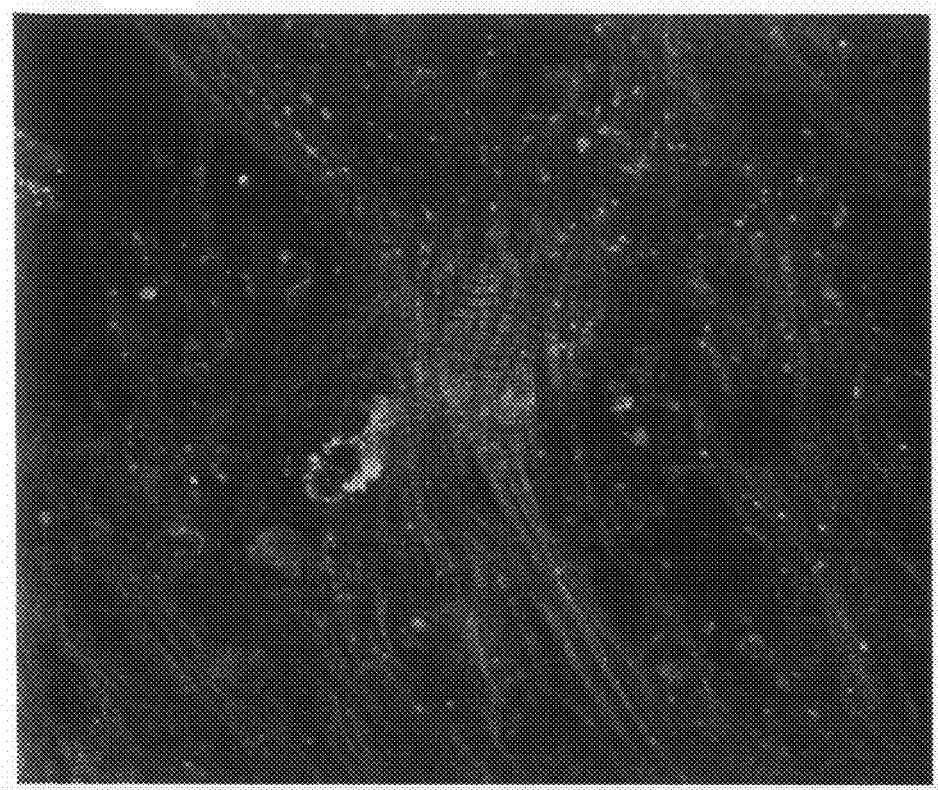
FIG. 5 shows a laser scanning confocal micrograph (A) of cardiac myocytes on a collagen scaffold of the present invention, stained with antibodies to F-actin and connexin 43, illustrating expression of connexin 43 along the sides and ends of the myocytes. Panels (B) and (C) are a stereo pair of laser scanning confocal micrographs of cardiac myocytes on a collagen scaffold of the present invention stained with an antibody to F-actin (Alexa 488 phalloidin). Multiple layers of cells with aligned fibrils can be seen when viewing the images with stereo viewing equipment.
Figure 5B:
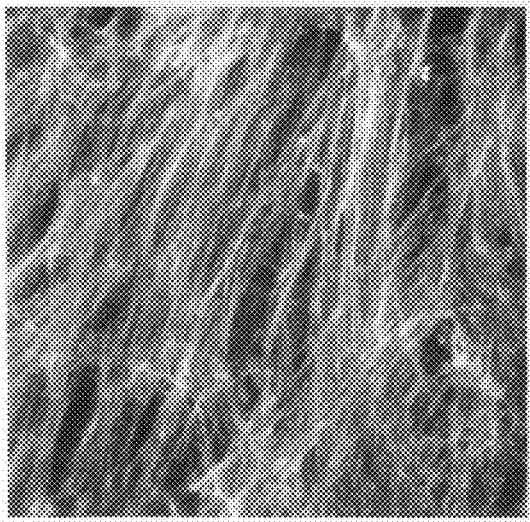
Figure 5C:
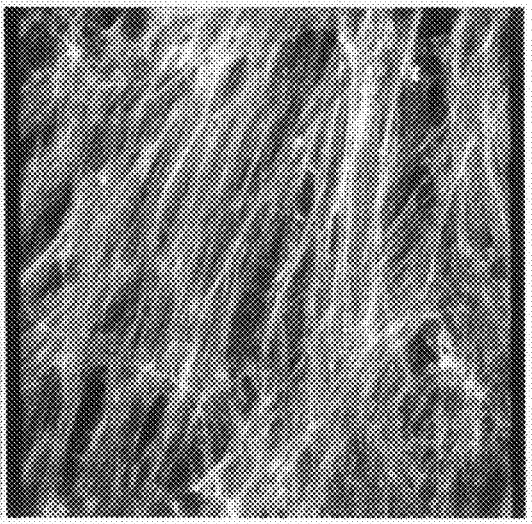

Characterization of Cardiac Myocytes in Collagen Tubes:

For confocal microscopy, tubes were sectioned longitudinally, fixed and stained for f-actin and connexin 43 (Chemicon MAB3068; 1:1000 dilution) as described by Price, R. L., et al., *Anat Rec,* 245:83-93 (1996); and Angst, B. D., et al., *Circ Res,* 80:88-94 (1997). FIG. 5 demonstrates a connexin 43 protein expression pattern similar to that described in vivo, where connexin 43 is distributed along the periphery of the cardiac myocyte and in cell-cell junctions (A). For stereo imaging, Z-series were collected at 1 μm intervals to a maximum depth of 80 μm. Reconstructed confocal microscopy Z-series through cardiac myocyte seeded tubes after 4 weeks in culture, shown in FIGS. 5 (B) and (C), show four to five layers of cardiac myocytes aligned in parallel with the collagen fibrils in the tube wall.

Cardiac myocyte seeded tubes were processed for transmission electron microscopy (TEM) as previously described in Price, R. L., et al., *Anat Rec,* 245:83-93 (1996). TEM images, like those in FIGS. 6 (A) and (B), demonstrate the presence of organized, aligned myofibrils (F), well-developed sarcomeres (not shown), Z-bands (Z), numerous mitochondria (M), cell:cell junctions (arrows in inset A), and attachment to collagen fibrils (arrows in inset B), characteristic of the cardiac myocyte phenotype seen in vivo.

Determination of Electrical Activity of Cardiac Myocyte Seeded Tubes:

Seeded tubes were measured for electrical activity by attaching two platinum wires at opposite ends of the tube, using a third wire as a reference in the surrounding media. The wires were shielded from interference by enclosing all but the distal end of each wire within a plastic casing. These electrodes were connected to an amplifier, an analog-to-digital converter, and finally to a computer where the signal was recorded. One-hundred seconds of electrical activity was collected for eight different tubes at 100 samples per second. The signal was then processed using a Fast Fourier transform algorithm to show the electrical activity of individual tubes. FIG. 7 (A) is a representative electrical signal recorded from a tube after 4 weeks in culture, and FIG. 7 (B) illustrates the Fast Fourier transform analysis of the electrical data, demonstrating a dominant frequency at 3.4 Hz. This corresponds to the contraction frequency of about 200 beats per minute obtained by visual observation and counting of contractions.

Example 4

This example demonstrates the use of the disclosed tissue scaffold for ventral hernia repair.

Collagen tubes can be made following the procedure described in Example 2, or according to any of the methods set forth in this disclosure. The collagen tubes are cut open longitudinally to form sheets, and a thin layer of collagen solution is streaked on the surface of the substrates and allowed to polymerize. This procedure results in a thin layer of collagen fibrils that are arrayed in parallel with one another along the direction that the collagen solution was streaked. Skeletal myoblasts were plated on the patterned collagen sheets. Over several days, the myoblasts continued to fuse and a series of uniformly arrayed, densely packed myotubes with morphology reflective of skeletal muscle developed.

The majority of the cells placed on the aligned collagen are MyoD positive myoblasts that fuse into multinucleate myotubes. Confocal microscopy of a phalloidin stained culture demonstrates parallel-aligned skeletal muscle cells with uniformly spaced sarcomeres. Located between the skeletal muscle cells are a population of fibroblast-like cells that are a mixture of myoblasts and fibroblasts that can produce collagen. To increase the thickness of the aligned skeletal muscle cultures and form a more tissue-like construct, the collagen sheets with aligned myotubes are placed in the Rotating Wall Bioreactor (RCCS) (Synthecon), and additional cells are seeded to achieve multilayering. It is possible to obtain as many as 40 layers of skeletal muscle cells in the RCCS.

In order to use these constructs for repair of ventral hernia, an experimental model of hernia in a rat is used. After achievement of general anesthesia, the animal's abdomen is opened and a 1 cm² midline abdominal wall defect is created. At this point, the engineered skeletal muscle tissue is surgically sewn into the defect and the abdomen is closed. Topical antimicrobials are placed on the incision and the animal is allowed to ascend from anesthesia. Intramuscular analgesics are administered as well as subcutaneous fluid boluses while the animal recovers. Tissue integration is monitored post operatively by clinically inspecting the surgical sight for signs of infection, bleeding, suture failure, and extrusion of viscera through the rectus abdominous, indicative of repair failure. Animals are sacrificed at specific time points and the tissue is evaluated for specific events known to occur throughout the wound healing process.

The implanted tissue is evaluated microscopically, monitoring normal wound healing processes, neovascularization, innervation, inflammation and infection. Inflammatory cells, tissue morphology and detection of angiogenesis are investigated using hematoxylin and eosin (H&E) stains. For this evaluation, 5 mm diameter punch biopsies of the interface between the native tissue and the repair material are obtained and serially sectioned. The sections are evaluated for clinically significant signs of rejection or infection such as extensive interstitial mononuclear cell infiltration and edema as well as mild interstitial hemorrhage and antibody-mediated rejection by the presence of significant foamy macrophage populations.

Neovascularization should be apparent on the H&E slides. Endothelial cells as well as the internal elastic lamina and vascular smooth muscle cells are identified for arterial vessels. The tunica intima, tunica media and vasa vasorum are identified for venous vessels. The presence of red blood cells within the vessels is a strong indication of their functionality. Collagen accumulation and location are evaluated using Masson's trichrome staining. Myoneural junctions should clearly display the myelinated nerve fiber approaching the skeletal muscle fiber. As the axon nears the muscle cell, it loses its myelin sheath and continues on as a non myelinated axon which can be visualized by Sevier-Munger staining for neural tissues. Motor end-plates should also be apparent using Gwyn-Heardman staining method described in the Color Atlas of Histology, 3$^{rd}$ ed. Baltimore: Lippincott Williams and Wilkins (2000).

The tissue at the repair site is also analyzed immunohistochemically for the temporal and spatial localization of growth factors VEGF, PDGF, and NGF within and around the repair. Two sets of the 2 mm biopsies are taken. One set is analyzed for growth factors by enzyme-linked immunosorbent assay (ELISA) to quantify the concentration of growth factors within the tissue (ELISA kits: VEGF and PDGF from R&D systems, NGF from Chemicon). The second set is fixed with paraformaldehyde, sectioned, and immunohistochemically stained for VEGF, PDGF and NGF using commercially available antibodies (R&D systems). The antibody staining is imaged using a laser scanning confocal microscope to localize the concentrations of growth factors spatially within the tissue using the methods of Germani. A., et al., *Am J Path.* 163(4):1417-1428 (2003). Briefly, samples are fixed in 4% paraformaldehyde overnight at 4° C. They are vibratome sectioned and stained with 488-phalloidin for f-actin, and immunohistochemically labeled using commercially-available antibodies. Serial sections are labeled with either VEGF, PDGF or NGF, one growth factor label per section. Secondary antibodies are labeled with Texas Red. Immunohistochemical visualization is performed using a Bio-Rad 1024 ES laser scanning confocal microscope.

Additionally, the tissue is evaluated mechanically for normal wound healing repair strength development. The indenter force required to puncture the abdominal repair is measured using an Instron® force measurement system. Measurements are made on the abdominal repair by resecting the entire abdominal wall free from the animal and placing it in ice cold Krebs Ringer solution with 30 mM 2,3-butanedione monoxime (BDM) to prevent dissection injury. Samples are mounted in a bath perfused with warm (37° C.) Krebs Ringer solution oxygenated by bubbling the solution reservoir with a 95% $O_2$/5% $CO_2$ mixture. The sample is placed in the stainless steel "picture frame" sample holder which clamps the sample along the edges in a plane parallel to the base of the Instron®) and perpendicular to the indenter. A 3 mm diameter spherical indenter is used to impinge on the center of the repair site. The sample is indented at a rate of 3.0 mm/sec. The force and displacement of the indenter and the peak force required to burst through the repair site are measured and recorded. Samples for mechanical testing are from animals that have not undergone punch biopsies. Data will be analyzed using ANOVA followed by pair-wise comparison.

All references cited in this specification, including without limitation all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinency of the cited references.

In view of the above, it will be seen that the several advantages of the invention are achieved and other advantageous results obtained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. An apparatus for producing a tubular tissue scaffold having aligned biopolymer fibrils and defining a tube wall about a luminal space, the apparatus comprising:
   a biopolymer gel dispersion feed pump;
   a counter-rotating cone extruder comprising an external rotating member having a cone-shaped cavity therethrough and an internal rotating cone which fits within the cone-shaped cavity of the external rotating member, wherein the external rotating member and the internal rotating cone terminate near the apex of the cones to form an annular-shaped exit port, the external rotating member and the internal rotating cone comprising a bearing-quality polymeric resin, and wherein the biopolymer gel dispersion feed pump is operably connected to the counter-rotating cone extruder such that the counter-rotating cone extruder produces a tubular tissue scaffold from the biopolymer gel dispersion exiting the exit port while providing an angular shear force across the wall of the tubular tissue scaffold;
   a liquid bath located to receive the tubular tissue scaffold from the counter-rotating cone extruder;
   a controlled atmosphere chamber enclosing the exit port of the counter-rotating cone extruder and the liquid bath; and
   a gas source that is interconnected to provide for the addition of gas to the luminal space of the tubular tissue scaffold exiting the exit port.

2. The apparatus according to claim 1, wherein the annular-shaped exit port has an outside diameter and an inside diameter, the difference between defining a width of an annular space of the tubular tissue scaffold.

3. The apparatus according to claim 2, wherein the outside diameter of the annular-shaped exit port is between about 1 mm and about 20 mm, and the width of the annular space is between about 0.1 mm and about 2 mm.

4. The apparatus according to claim 1, wherein the external rotating member and the internal rotating cone are operably connected to one or more drive motors that can spin the external rotating member and the internal rotating cone about a common axis but in opposite directions.

5. The apparatus according to claim 1, wherein the external rotating member and the internal rotating cone are operably connected to the same drive motor.

6. The apparatus according to claim 4, wherein the one or more drive motors can be adjusted to vary the speed at which the external rotating member and the internal rotating cone rotate.

7. The apparatus according to claim 4, wherein the rotational speed of the external rotating member and the internal rotating cone can be varied between about 1 rpm and 1800 rpm.

8. The apparatus according to claim 1, wherein the biopolymer feed pump can be adjusted to vary the rate at which biopolymer is fed to the tube-forming device.

9. The apparatus according to claim 1, wherein the liquid bath is located below the extruder exit port, whereby tubular tissue scaffold exiting the extruder falls into the bath by force of gravity.

10. The apparatus according to claim 9, wherein the surface of the liquid bath is located a defined distance below the extruder exit port.

11. The apparatus according to claim 10, wherein the defined distance is between about 0.25 centimeter and about 60 centimeters.

12. The apparatus according to claim 1, wherein the gas source can provide a mixture of air and ammonia.

13. The apparatus according to claim 12, wherein the mixture of air and ammonia is about a 50:50 mixture by volume.

14. The apparatus according to claim 1, wherein the controlled atmosphere chamber is filled with a gas mixture comprising air and ammonia.

15. The apparatus according to claim 14, wherein the gas mixture comprises a mixture of about 50:50 air and ammonia by volume.

16. The apparatus according to claim 1, wherein the liquid bath comprises water having sufficient ammonia absorbed therein to bring the pH of the water to between about 9 and 11.

17. The apparatus according to claim 1, wherein the external rotating member and the internal rotating cone comprise an acetal polymeric resin.

18. The apparatus according to claim 1, wherein bearings are excluded from the counter-rotating cone extruder.

19. The apparatus according to claim 1, wherein the gas source is interconnected to provide for the addition of gas to the luminal space of the tubular tissue scaffold exiting the exit port and to the controlled atmosphere chamber.

* * * * *